(12) United States Patent
Green et al.

(10) Patent No.: US 8,969,549 B2
(45) Date of Patent: Mar. 3, 2015

(54) ANTIOXIDANT SMALL MOLECULES AIMED AT TARGETING METAL-BASED OXIDATIVE STRESS IN NEUROGENERATIVE DISORDERS

(71) Applicant: Texas Christian University, Fort Worth, TX (US)

(72) Inventors: Kayla Nalynn Green, Fort Worth, TX (US); Kimberly Marie Lincoln, Fort Worth, TX (US); Paulina Gonzalez, Fort Worth, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

(21) Appl. No.: 14/156,683

(22) Filed: Jan. 16, 2014

(65) Prior Publication Data

US 2014/0206862 A1    Jul. 24, 2014

Related U.S. Application Data

(63) Continuation-in-part of application No. 14/105,435, filed on Dec. 13, 2013.

(60) Provisional application No. 61/754,012, filed on Jan. 18, 2013.

(51) Int. Cl.
*C07D 487/00* (2006.01)
*C07D 471/08* (2006.01)
*C07D 403/14* (2006.01)
*C07D 409/06* (2006.01)

(52) U.S. Cl.
CPC ............ *C07D 471/08* (2013.01); *C07D 403/14* (2013.01); *C07D 409/06* (2013.01)
USPC ........................................................ 540/471

(58) Field of Classification Search
CPC .................................................... C07D 487/00
See application file for complete search history.

(56) References Cited

U.S. PATENT DOCUMENTS

2004/0204344 A1   10/2004   Huang
2011/0110850 A1   5/2011   Barnham et al.

FOREIGN PATENT DOCUMENTS

WO   WO2014113624 A1 *   7/2014

OTHER PUBLICATIONS

Richardson, T., et al. "An N-Heterocyclic Amine Chelate Capable of Antioxidant Capacity and Amyloid Disaggregation." ACS Chem Neurosci. (2012), vol. 3, pp. 919-927.*
Costa, J., et al. "Metal Complexes of Macrocyclic Ligands Containing Pyridine." Inorg. Chem. (1993), vol. 32, pp. 5257-5265.*
Riechers, A., et al. "Detection of Protein Phosphorylation on SDS-Page Using Probes with a Phosphate-Sensitive Emission Response." Bioconjugate Chem. (2009), vol. 20, pp. 804-807.*
Paul A. Adlard, et al.; "Metal Ionophore Treatment Restores Dendritic Spine Density and Synaptic Protein Levels in a Mouse Model of Alzheimer's Disease"; article; 7 pages; Mar. 2011, vol. 6, Issue 3, e17669 PLoS One; www.plosone.org.
Noel G. Faux, et al.; "PBT2 Rapidly Improves Cognition in Alzheimer's Disease: Additional Phase II Anaylses"; Journal of Alzheimer's Disease; 9 pages; IOS Press; copyright 2010.
Peter E. Crouch, et al.; "The Alzheimers Therapeutic PBT2 Promotes Amyloid-β Degradation and GSK3 Phosphorylation Via a Metal Chaperone Activity"; Article; Journal of Neurochemistry; 11 pages; copyright 2011; International Society for Neurochemistry.
Alaina S. Detoma, et al.; "Myricentin: A Naturally Occurring Regulator of Metal-Induced Amyloid-β Aggregation and Neurotoxicity"; ChemBioChem; 4 pages; copyright 2011; Wiley-VCH Verlag GmbH & Co. KGaA, Weinheim.
Lincoln, et al., An Antioxidant Chelate in Response to Metal-Induced Amyloid Aggregation in Alzheimer's Disease (2013); http://www.srs.tcu.edu/previous_posters/Chemistry/2012/277-Lincoln-Green.pdf.

* cited by examiner

*Primary Examiner* — Noble Jarrell
*Assistant Examiner* — John S Kenyon
(74) *Attorney, Agent, or Firm* — Charles D. Gunter, Jr.

(57) ABSTRACT

Amine chelates capable of antioxidant capacity and amyloid disaggregation are shown which may be useful in targeting metal-based oxidative stress in neurodegenerative disorders. Pyclen, a backbone commonly investigated for contrast agent imaging, may be repurposed as an anti-oxidant chelator for disaggregating amyloid. The antioxidant capacity of pyclen is enhanced dramatically via conversion of the pyridine backbone to a pyridol with cellular studies showing superior antioxidant capacity while retaining chelation ability to protect amyloid from metal ions aggregation and also disaggregate amyloid aggregates. Another family of molecules based upon hybrid heterocyclic amine ligands is also presented.

1 Claim, 11 Drawing Sheets

ANTIOXIDANT SMALL MOLECULES AIMED AT TARGETING METAL-BASED OXIDATIVE STRESS IN NEUROGENERATIVE DISORDERS

CROSS REFERENCE TO RELATED APPLICATIONS

The present application is a continuation-in-part of earlier filed Ser. No. 14/105,435, filed Dec. 13, 2013, entitled "Antioxidant Small Molecules Aimed at Targeting Metal-Based Oxidative Stress in Neurodegenerative Disorders", which, in turn, claimed priority from a provisional application, Ser. No. 61/754,012, filed Jan. 18, 2013, entitled "Antioxidant Small Molecules Aimed At Targeting Metal-Based Oxidative Stress In Neurodegenerative Disorders", by the same inventors.

BACKGROUND OF THE INVENTION

1. Field of the Invention

The present invention relates the development of potent biomodal antioxidant small molecules capable of beta-amyloid prevention and disaggregation and for targeting metal-based oxidative stress in neurodegenerative disorders.

2. Description of the Prior Art

Alzheimer's disease (AD) is a debilitating disease that affects over 5.4 million people currently, at an annual cost exceeding 180 billion dollars in the U.S. alone. Physiological and molecular features include the deposition of beta-amyloid (Aβ) plaques, elevated levels of transition metals and oxidative stress. The exact mechanism leading to AD is still not-established, although amyloid is a component in many hypotheses proposed to date. Recent attention has implicated metal ions in the cascade leading to the physiological and pathological hallmarks of AD thus forming the "Metal Hypothesis of Alzheimer's Disease".

Transition metals are trace elements vital for normal biological function because they serve as structural drivers, cofactors or reactive centers in proteins and enzymes. Fenton chemistry is defined by the oxidation of redox active metal ions in their reduced from, such as Fe(II) or Cu(I), with $H_2O_2$ to produce radicals that are known to cause DNA oxidation, disruption of mitochondrial membrane potentials, lipid peroxidation. Redox chemistry of these elements is tightly regulated throughout biology via regulatory and chaperone systems, so that protein modification, in conjunction with Fenton chemical reactions, producing cellular oxidative stress will be avoided. Disruptions or alterations in the redox potential of metal-ion regulatory systems have therefore been implicated in a number of disease states to date which include: Huntington's, Alzheimer's, and Parkinson's, Lou Gehrig's disease, as well as macular degeneration and Freidrich's ataxia. For example, a histidine rich binding site has been identified in $A\beta_{1-40}$ or $A\beta_{1-42}$. Insoluble beta-amyloid plaques (Aβ) have increased levels of copper, zinc and iron, while intracellular copper stores are deficient in AD patients. Metal ion chelation by amyloid plaques gives rise to concomitant free radical generation, resulting in neuronal death. Furthermore, increased levels of oxidative stress have been, in-part, attributed to alterations in the expression of superoxide dismutase, as well as protein metal-ion chaperones. Modifications in the levels of metal-ion chaperone expression associated with the signal transduction pathway of glutamate receptors, for example, have also been noted with concomitantly higher levels of cleaved amyloid precursor protein to produce $A\beta_{1-40}$ or $A\beta_{1-42}$. Finally, aged populations naturally exhibit increased levels of ROS due to decreased levels of antioxidants such as melatonin, resulting in higher levels of oxidative stress. However, AD models suggest more exacerbated levels of ROS, thus resulting in AD progression.

There is no effective or preventative protocol prescribed for AD, nor have proposed therapies found success in symptom alleviation neurodegenerative decline associated with AD. Many hypothetical pathways of AD have been targeted, one taking aim at the metal-based hypothesis proposed by Bush et al. Synthetic targets focused on inhibiting the interactions of Aβ with metal ions, along with atypical metal ion homeostasis are limited by ion specificity, an inability to cross the blood brain barrier (BBB), and/or biological compatibility. A compound finding exception to these roadblocks has been evaluated in Phase II clinical trials. The chelator clioquinol (CQ) provided improved cognition in mouse models, but its widespread use has been terminated by the adverse side effect of subacute myelo-optic neuropathy. The positive effects exhibited by CQ encourage synthetic chemists to pursue the chelator strategy as a route to potentiating the cognitive decline associated with metal-ion mis-regulation and plaque deposition. A second generation congener of CQ, PBT2, has been produced and is in Phase II clinical trials. Studies of this compound showed improved cognition in AD transgenic mice, and demonstrated positive effects on the learning and memory in AD patients. In contrast to this agent serving as a chelator as utilized in the sense of typical metal-overload disorders, i.e., removing excess metal, the authors have shown that these compounds can serve as neuromodulators by restoring the metal-ion imbalance for neurochemical communication pathways involved in synaptic activity. When the "lost" metal ions that lead to Aβ deposition are rescued by these synthetic chaperones, their activities in the communication pathways are restored, and Aβ clearance is elevated.

With these results, the present invention has as one object the pursuit of biologically compatible transition metal-ion ligands as therapy for AD and other related neurodegenerative diseases.

SUMMARY OF THE INVENTION

The misregulation of metal ions is known to produce ROS that lead to neurological degradation associated with Alzheimer's disease in addition to their interaction precipitating amyloid plaques. A molecular system capable of bimodal modulation of the metal-ions in amyloid as well as regulation of the increased levels of ROS would prove useful in combating this disease. To address these issues, Applicants have shown that compound 1, below, a backbone previously investigated for contrast agent imaging, may be repurposed as an anti-oxidant chelator for disaggregating amyloid. 1 will be compared to compounds 2-4 below in the detailed description of the invention which follows:

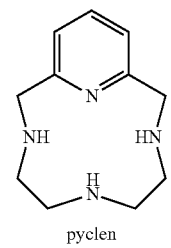 [SMILES: c1cc2nc(c1)CNCCNCCNC2]

pyclen

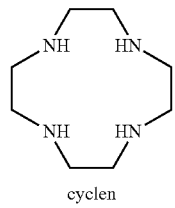 [SMILES: C1CNCCNCCNCCN1]

cyclen

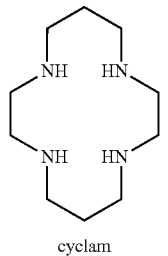

cyclam

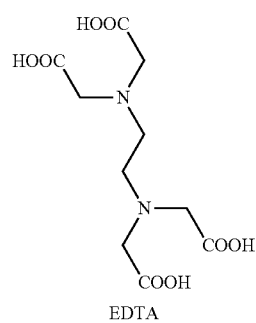 [SMILES: O=C(O)CN(CCN(CC(=O)O)CC(=O)O)CC(=O)O]

EDTA

| log K constants | | | |
|---|---|---|---|
| $Cu^{II}$ | 20 | 23 | 27 | 9.18 |
| $Zn^{II}$ | 14 | 16 | 15 | 8.41 |

Spectroscopic and TEM/SEM imaging studies show the ability of 1 to protect amyloid from copper ions and also disaggregated amyloid aggregates as well. The antioxidant assays show that 1 has antioxidant capacity in vivo and protective capabilities via Calcein AM studies. The DFT studies and direct reactions with $H_2O_2$ show that the pyridine backbone is the key to this ability.

In addition, Applicants have learned that the antioxidant capacity of 1 can be enhanced dramatically in the hydroxylated version of the pyclen molecule via conversion of the pyridine backbone to a pyridol to produce 2 shown below:

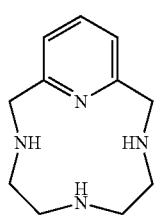

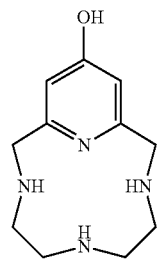

Cellular studies show superior antioxidant capacity while retaining chelation ability to protect amyloid from metal ions aggregation and also disaggregate amyloid aggregates. Direct reactions with $H_2O_2$ show that the pyridol backbone is the key to this ability due to the formation of di-keto species of 2.

A further aspect of the present invention is concerned with the synthesis of "hybrid" heterocyclic amines, which can act as ligands that can rescue the copper misplaced in the plaques, thus restoring solubility of these aggregates. These same compounds are also designed to quench radicals generated by oxygen based species as a means to reducing neuronal damage. The following compounds are exemplary:

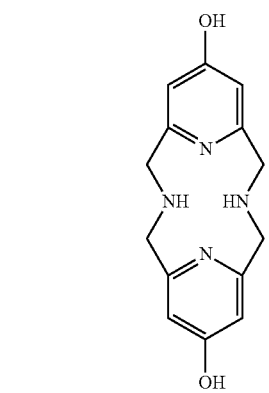

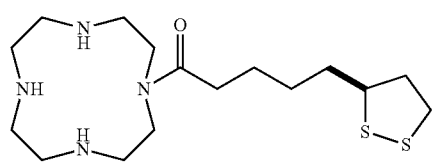

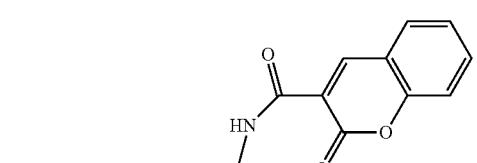

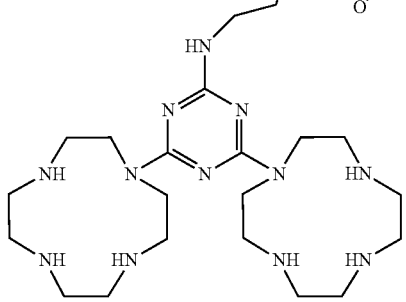

Additional objects, features and advantages will be apparent in the written description which follows.

DETAILED DESCRIPTION OF THE INVENTION

The embodiments herein and the various features and advantageous details thereof are explained more fully with reference to the non-limiting embodiments that are illustrated in the accompanying Figures and detailed in the following description. The examples used herein are intended merely to facilitate an understanding of ways in which the invention herein may be practiced and to further enable those of skill in the art to practice the invention. Accordingly, the examples should not be construed as limiting the scope of the claimed invention.

Part I:

Utilizing a rational design approach, the initial part of this work focuses on the use of pyclen (1) shown in Chart 1 as a metal-ion passivation and antioxidant agent based on this ligand's specific metal-ion binding affinity for copper(II) and zinc(II) along with built-in antioxidant functionalities. The ligand is the backbone to PCTA, a potential MRI contrast agent explored in recent years and has been repurposed for Applicant's work.

CHART 1

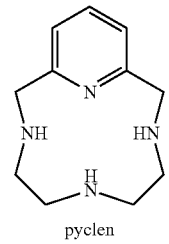

pyclen

1

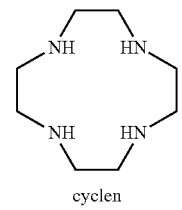 [SMILES: C1CNCCNCCNCCN1]

cyclen

2

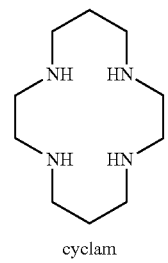 [SMILES: C1CNCCNCCCNCCNC1]

cyclam

3

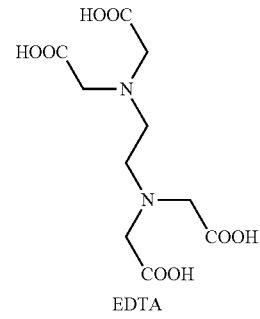 [SMILES: O=C(O)CN(CCN(CC(=O)O)CC(=O)O)CC(=O)O]

EDTA

4

| | log K constants | | | |
|---|---|---|---|---|
| $Cu^{II}$ | 20 | 23 | 27 | 9.18 |
| $Zn^{II}$ | 14 | 16 | 15 | 8.41 |

Figure 1:
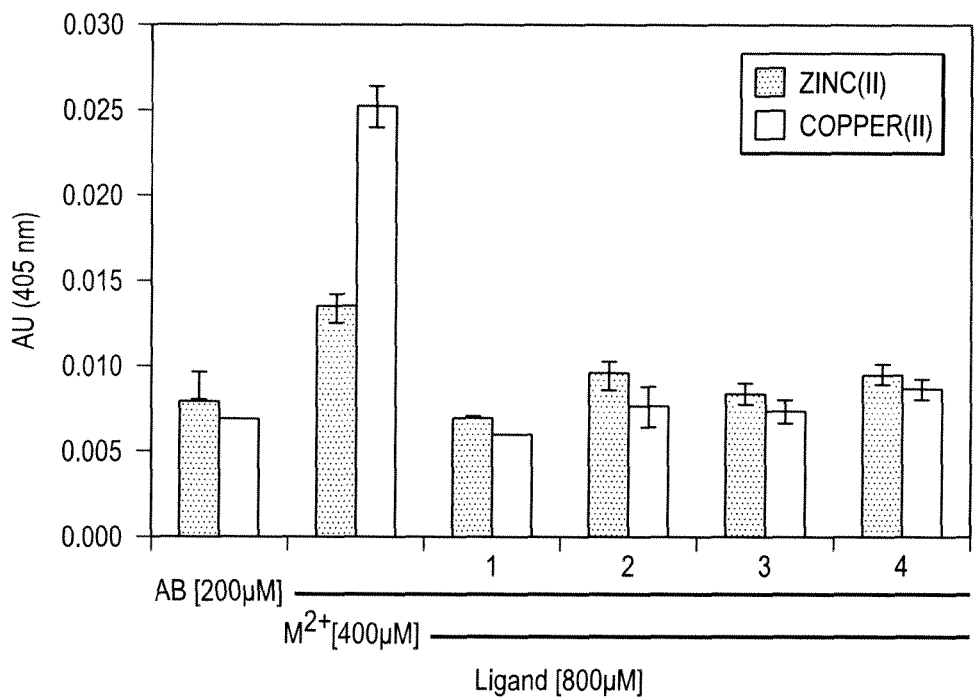
FIG. 1 is a Turbidity Assay graph showing disaggregation of amyloid plaques upon incubation (24 hours at 37° C.) with 1-4 described in the detailed discussion which follows.

Metal ions (copper and zinc) bind to a histidine rich domain in amyloid producing Aβ in the form of insoluble plaques. This process has been comprehensively studied and described in a number of recent reviews. The aggregation of amyloid can be followed by simple spectroscopic techniques such as turbidity and tyrosine fluorescence studies. These methods were used to investigate the ability of 1 to dissociate pre-formed amyloid aggregates upon addition of metal ions, as well as prevent amyloid aggregation. As shown in FIG. 1, copper (II) or zinc (II) ion addition to a solution of Aβ$_{1-40}$ results in a visibly turbid solution which scatters light with a consequential increased absorbance signal, using absorption spectrophotometry. The aggregation observed upon metal ion addition can be reversed by co-incubation of 1 for 4 hours, indicating dissolution of the amyloid aggregates. A visible dissolution of the peptide solution is concomitant to the decrease in absorbance signal. For comparison, this experiment was repeated with 2 and 3 (Chart 1) previously studied by Hindo et. al as Aβ dis-aggregating agents, which Applicant's studies corroborate. The known open-chain chelator EDTA was used as a positive control, and Applicant's studies demonstrated that all ligands were equally successful in disrupting turbidity of the aggregated amyloids. In a similar study, the protective capability of 1 was compared to compounds 2-4 (Chart 1). The ligands (1-4) were first co-incubated with amyloid and then metal-ions were added. The ligands displayed an ability to prevent metal-induced aggregation of amyloid upon exposure to copper (II) or zinc (II) salts.

Figure 2:
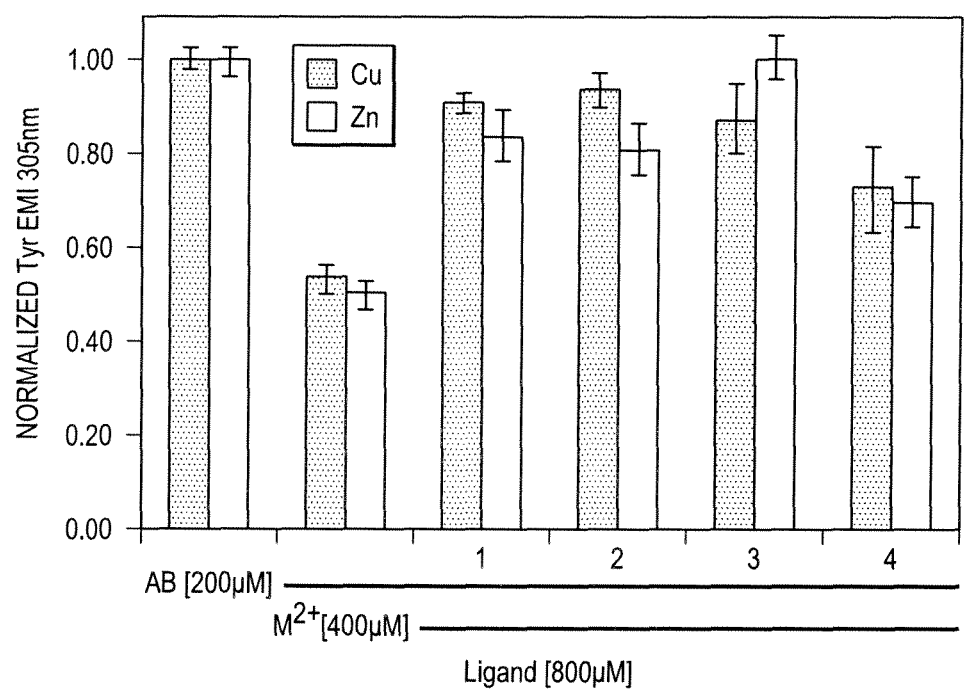
FIG. 2 is a graph showing the addition of ligands 1-4 to aggregated Aβ results in reconstitution of Tyr[10] fluorescence which was decreased due to aggregate formation.

To further determine the capability of 1 to prevent or disrupt metal-ion induced amyloid aggregation, Applicant's studied Tyr fluorescence intensity. Recent reports have also utilized the natural fluorescence of the native $Tyr^{10}$ in the $A\beta_{1-40}$ sequence to study the conformational dynamics of amyloid folding as it relates to AD and/or production of $H_2O_2$. As $Tyr^{10}$ is located within proximity to the metal binding pocket in $A\beta_{1-40}$ the fluorescence intensity of the phenolic side chain decreases during the folding process due to environmental changes that occur locally. This work was supported by circular dichroism spectra, which verified that fluorescence intensity decreased as the conformation of amyloid changed to beta-sheets. Yang and colleagues showed that this spectroscopic marker could be used to follow the folding induced by the addition of copper ions to amyloid, and related the production of $H_2O_2$ to this process. Applicant's hypothesis was that Tyr fluorescence intensity should be restored to control levels upon addition of compounds 1-4 (Chart 1) to a solution of pre-formed metal aggregates, as shown below in FIG. 2. These results are consistent with the turbidity studies presented above. Similar results were also obtained for amyloid samples co-incubated with 1-4 prior to metal ion addition. That is, the ligand chelates show a protective capability by preventing the production of aggregates as evidenced by higher Tyr fluorescence signal compared to the control of amyloid co-incubated with copper(II) or zinc(II), which showed a large decrease in signal intensity after 24 hours.

Figure 3:
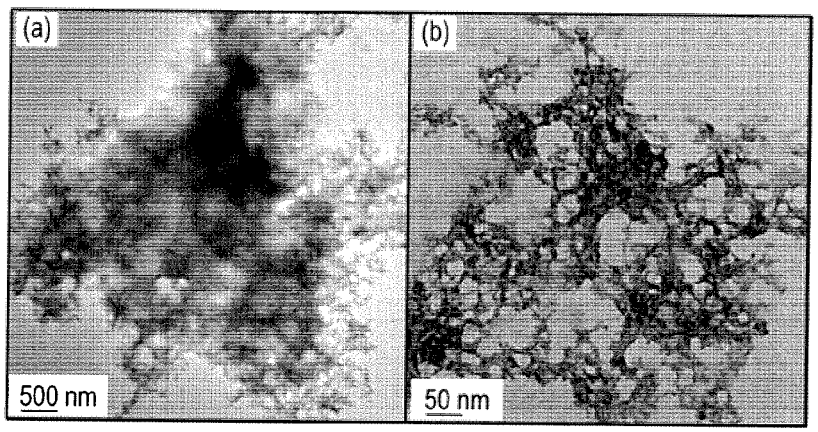
FIG. 3 is an illustration of TEM Images showing (a) copper induced aggregation of amyloid and (b) its dissolution by 1.

Transmission electron microscopy (TEM) and Scanning Electron Microscopy (SEM) were utilized to study the morphology of the aggregates with and without chelators, as well. The TEM images shown in FIG. 3 demonstrate that compound 1 decreases the amyloid aggregate size by 1-2 orders of magnitude compared to the copper aggregates. Grid (a) shows the large aggregates formed by the addition of metal ions to amyloid (scale 500 nm). Aliquots from the stock used to make grid (a) were then incubated with 1 for 12 hours and then prepared for microscopy. The sizes of the aggregates upon treatment with 1 are an average of 1-2 orders of magnitude smaller and observably more diffuse, as shown in grid (b). SEM images also confirm the ability of the chelates to affect aggregate size as well.

As increased levels of ROS are associated with AD, Applicant's set out to investigate the antioxidant character of 1 compared to the heterocycles 2 and/or 3. Initially, Applicant's showed that 1 was capable of preventing the formation of the ABTS. radical most effectively compared to 2-4 at ligand concentrations of 100 μM. These results were standardized against Trolox (a known antioxidant) with compound 1 providing 0.4 Trolox equivalents and compounds 2-4 resulting in values of 0.23, 0.11 and 0.15 respectively. Moreover, many of the pathways proposed to produce ROS leading to AD pathology involve metal ions. Applicant's therefore utilized the Cu-ascorbate redox system, Scheme 1, as a model to determine if the ligands could halt copper based redox activity under aerobic conditions:

Scheme 1. Redox cycling of copper in the presence of oxygen and ascorbate to produce OH·.

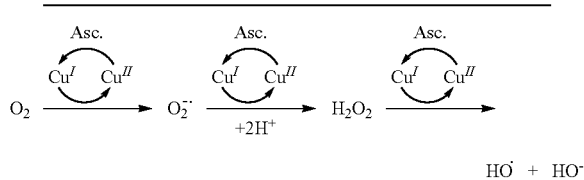

Figure 4:
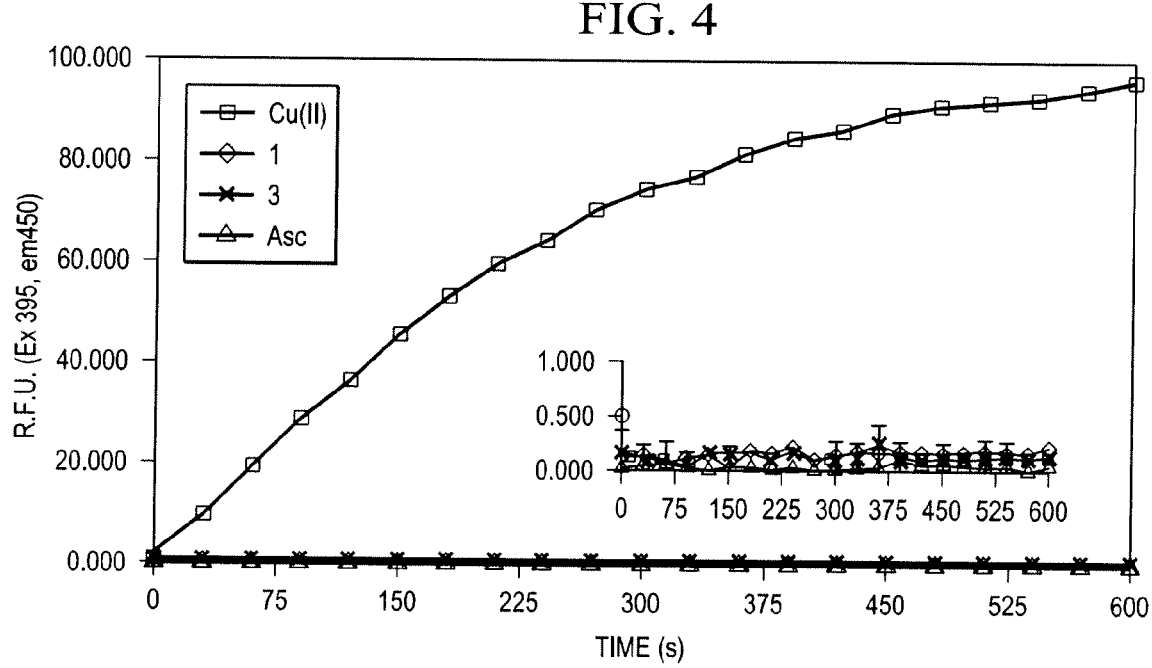
FIG. 4 is a graph showing Fluorescence intensity of 7-hydroxy-CCA after incubation of CCA [100 uM] and ascorbate [300 uM] with $Cu^{II}$(■)[40 uM].

This system is a useful model for studying the brain, as high levels of oxygen and ascorbate are present. Faller and co-workers employed this system to investigate the redox chemistry of amyloid systems with Cu. Coumarin-3-carboxylic acid (CCA), which generates fluorescent 7-hydroxy-CCA in the presence of hydroxyl radicals, was used to quantify the reduction of oxygen by copper redox-cycling in the presence of ascorbate. FIG. 4 shows that copper and ascorbate generate OH. as measured by 7-hydroxy-CCA which increases linearly for the first 5 minutes, and then plateaus around 10 minutes. This process is prevented entirely as shown in the inset of FIG. 4 when compounds 1 or 3 are co-incubated with the Cu-ascorbate system, indicating these ligands are capable of halting copper redox cycling via metal complexation. Next, the ability of 1 to halt hydroxyl generation was compared to $A\beta_{1-40}$, in which Faller reports a decrease the Cu-Ascorbate redox cycle. The Cu-ascorbate system was initially co-incubated with CCA for two minutes showing an increase in fluorescent signal as expected. At this point either 1 or $A\beta_{1-40}$ were added to the Cu-ascorbate system, resulting in a leveling of the 7-hydroxy-CCA signal. This indicated that the addition of 1 or AB1-40 was able to halt the copper redox cycling due chelation of the metal-ion. This redox silencing was verified by the addition of ascorbate to Cu(1) or Cu($AB_{1-40}$) in the presence of CCA resulting in absence of a fluorescent signal during the 10 minute timescale.

Figure 5:
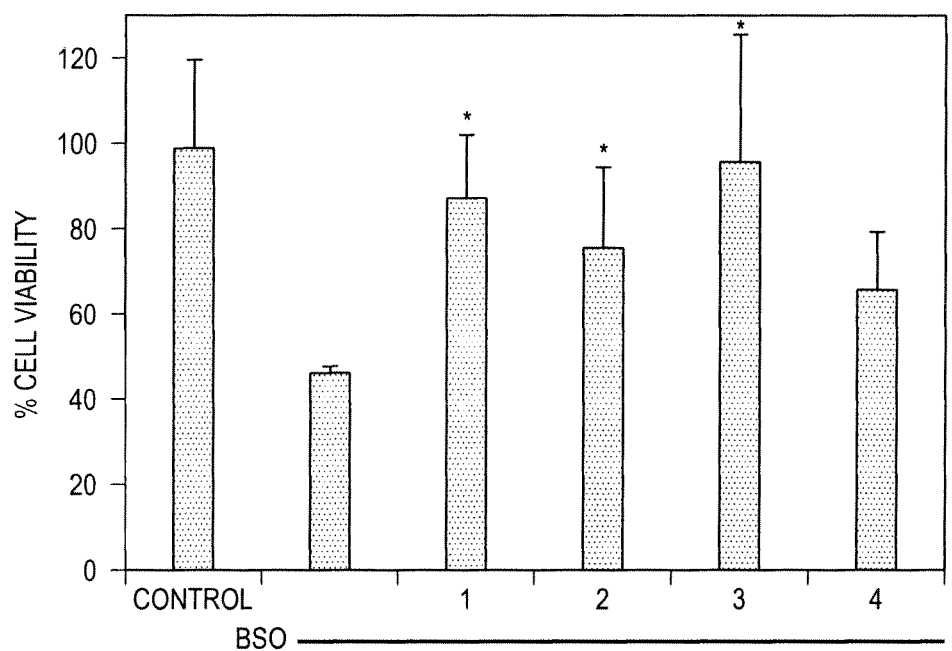
FIG. 5 is a graph showing a Calcien AM viability assay of FRDA cells after 48 hour exposure to BSO [1 mM] with 1-4 [1 nM final].

Cellular studies were then carried out to evaluate the intracellular efficacy and toxicity of compound 1 (Chart 1). Preliminary screens compared the cell viability of compounds 1-4 in an FRDA cell line (Fibroblasts from a Friedreich's Ataxia patient) and ability to negate oxidative stress. FRDA cells have higher levels of ROS due to mitochondrial misfunction associated with frataxin expression and therefore serve as a good model for ROS protection. FIG. 5 shows the normalized results of cell (FRDA) viability studies with compounds 1-4 at 1 nM final concentration. Calcein AM, a non-fluorescent, hydrophobic compound that easily permeates intact, live cells, was used as an indicator for cell viability. Calcein AM is hydrolyzed by intracellular esterases producing calcein, a hydrophilic, strongly fluorescent compound that is well-retained in the cell cytoplasm. Compared to the control containing untreated cells, incubation with either compound 1 or 3 exhibited >85% cell viability at the concentration studied, a statistically significant increase from cells treated with BSO-alone, which had a cell viability of ~45% compared to control cells. Compounds 2 and 4 were less efficatious, but still provide cell viability of greater than 60%. These results confirm that the heterocyclic compounds are compatible for use in cells by providing protection against oxidative stress induced by BSO. Moreover, the addition of the pyridine ring (1) into the heterocylic core does not induce cell death and, in fact, prevents ROS induced cell death most effectively.

The antioxidant activity of compound 1 compared to compounds 2-3 (Chart 1) was then studied using the cell-permeable fluorophore 2,7'-Dichlorodihydrofluorescin diacetate (DCFH-DA) as an indicator for ROS. DCFH-DA diffuses into cells and is deacetylated by cellular esterases to non-fluorescent 2',7'-Dichlorodihydrofluorescin (DCFH). This species is subsequently oxidized to the highly fluorescent 2',7'-Dichlorodihydrofluorescein (DCF) species in the presence of ROS. The fluorescent intensity is directly proportional to the amount of ROS present in cell cytosol. BSO (2-amino-4-(butylsulfonimidoyl)butanoic acid) was used to inhibit the first step of de novo glutathione synthesis, allowing us to observe the elevated intra-cellular [ROS] are thereby observed.

Figure 6:
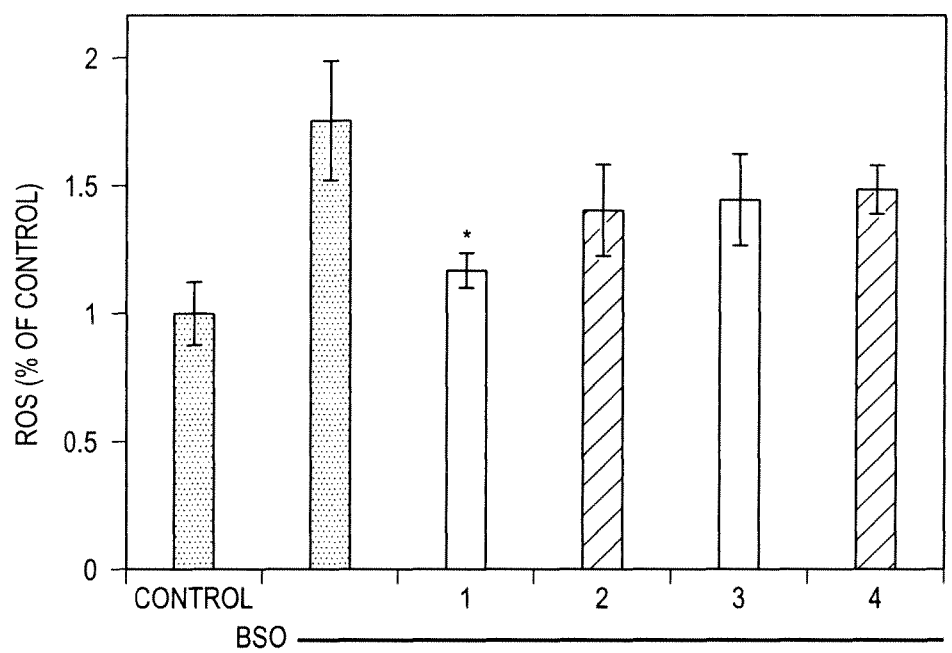
FIG. 6 is a graph showing DCFH-DA fluorescent response in FRDA cells after 12 hours exposure to BSO [1 mM] with 1-4 [4 nM].
Figure 7:
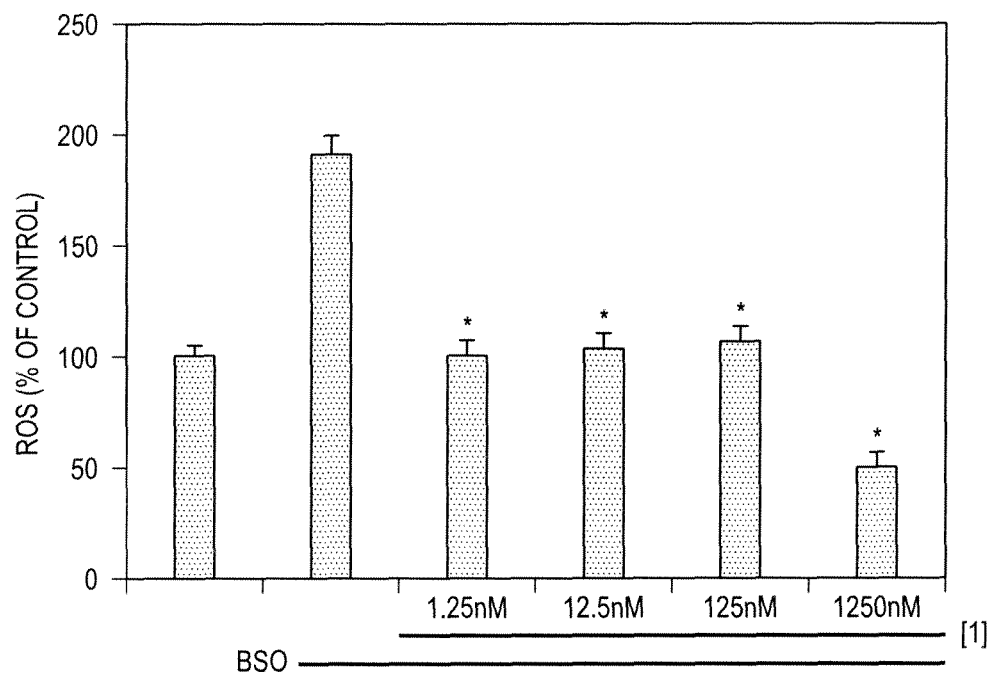
FIG. 7 is a graph of DCFH-DA fluorescent response in FRDA cells after 12 hours exposure to BSO [1 mM] showing dose dependence with 1.
Figure 8:
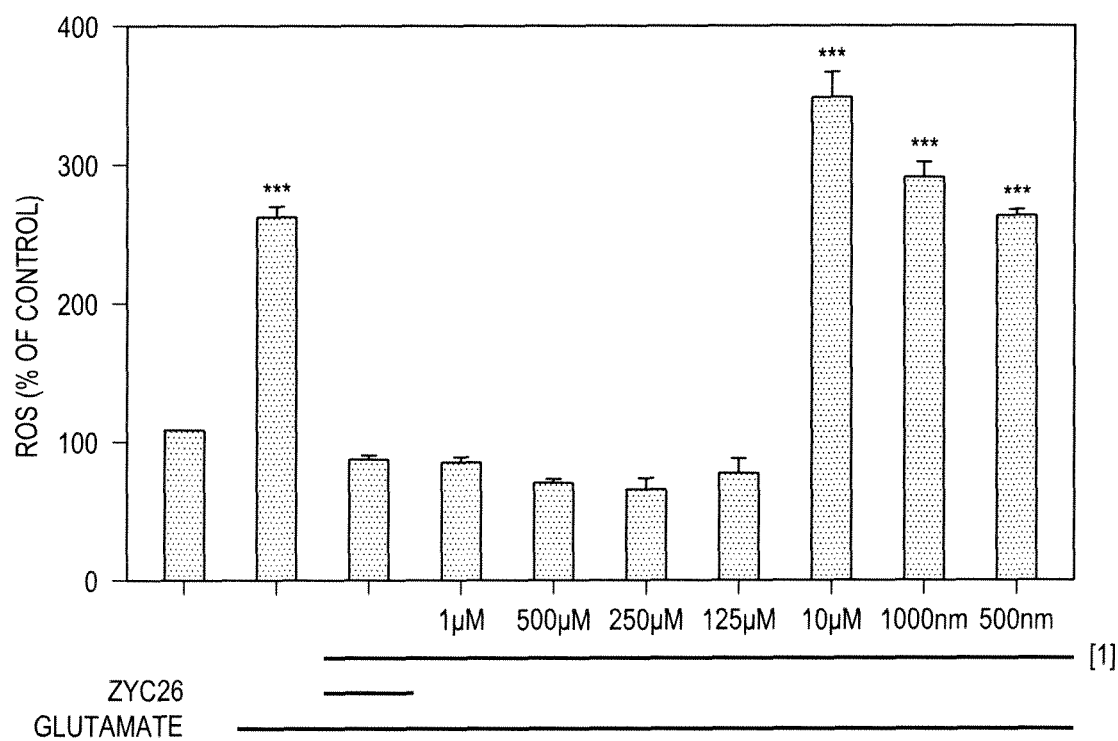
FIG. 8 is a graph of DCFH-DA fluorescent response to chelator 1 in HT-22 cell line.

The results of DCFH-DA cell culture assay shown in FIG. 6 indicate that 1 is the most effective antioxidant at low nM concentrations, significantly attenuating the ROS produced by BSO, with only a 15% increase of ROS over the negative control (media) when compared to 2-4. These results are compared to the positive control BSO-treated cells, with a nearly 1.8 fold increase in ROS. FIG. 7 shows that 1 is an effective antioxidant in the 1.25 nM to 1.25 µM range for the FRDA cell line as well. These results are consistent with results from the Trolox antioxant assay where it was noted that pyclen shows a superior antioxidant activity with and without metal ions present. This was repeated in a neuronal cell line (HT-22) and 1 showed antioxidant nature in the 1 mM-125 uM range (FIG. 8) with a glutamate assault which results in cell death by oxidative glutamate toxicity.

A comparison of these results with the cell viability studies discussed above show that the pyridine ring of compound 1 is responsible for the antioxidant capacity observed. The heterocyclic compounds 2 and 3 which showed cell viability congruent to 1 with BSO assault (FIG. 4) are structurally similar to 1 except for the pyridine ring. While 1-3 are all largely capable of preventing cell death induced by BSO, ligand 1 is capable of reducing ROS to the greatest extent, thus resulting in the most effective protective capacity. Applicants attribute this to the pyridine core. It is further postulated that the ability to prevent BSO induced cell death is a result of metal-ion scavenging capacity of these ligands 1-3. An interesting feature to be noted from these cellular studies is the fact that compound 1 is capable of entering cells and does not appear to interrupt the vital functions of cytosolic metalloenzymes via extraction metal ions from those functionalities.

Applicants have postulated that the observed antioxidant activity of compound 1 (Chart 1) is structurally correlated with the pyridine backbone, as evidenced by the radical studies and incubation of ligands with cells in the DCFH-DA cell culture assays presented above. Schugar and Orvig et al. have each reported antioxidant activity with pyridine like aromatic chelators in separate studies as well. The Weighardt group has computationally and spectroscopically studied bipyridine-based chelates, and their studies prove that the lowest unoccupied molecular orbital (LUMO) of the metal derivatives are composed of mainly ligand π-character.

Applicants have observed pyclen to be antioxant in the presence of copper ions, this methodology was applied to compounds 1-3 and their $Cu^{II}$ derivatives using DFT (B3LYP, 6-311 G (d,p for copper complexes)) to show that the LUMO orbital of 1 and Cu-$1^{2+}$ is largely centered on the pyridine ring. It can be shown that the HOMO of 1 has more electron density on the nitrogen atoms and the LUMO of 1 is composed of >90% π-character as compared to 2 and 3 which have density dispersed throughout. Moreover, the HOMO orbital of 1 is higher in energy compared to 2 as well. The other heterocyclic ligands 2-3 lack these features, i.e. the LUMO being antibonding character alone. Ligands 2 and 3 lack this component and therefore have the LUMO orbital spread throughout the ligand set in an anti-bonding orbital centered on the nitrogen atoms trans to one another, making reactivity less favored.

While not wishing to be bound by any particular theory, these characteristics of compound 1 likely stem from the fact that heterocycles containing aromaticity are reported to be highly reactive toward radicals produced via radiolysis of water and naturally react with the heterocycles by addition. Pyridine containing analogs have been reported in the past in the literature to be potent antioxidants, which is attributed to the electron deficient nature of the pyridine ring, with potency increasing as electron attracting groups are added onto the ring. Such reactivity is well documented, that is pyridine based compounds are known to produce N-oxides upon incubation with $H_2O_2$. To further support this, compounds 2 and 3 lack the pyridine ring but retain the secondary amines in the heterocyclic core and show little potency in the assays presented. The secondary amines, therefore, are less prone to produce N-oxides than the pyridine backbone. Interestingly, 2-3 do show a degree of anti-oxidant capacity which Applicant's postulate to be an effect of the redox tuning of the ligands on the copper ion, rather than ligand composition itself.

Part II:

The foregoing work led to the search for additional molecules having enhanced antioxidant power, compared to the parent 1, while retaining the anti-aggregate capacity. The second part of this work focuses on the use of compound 2 below (Chart 2) as a metal-ion passivation and antioxidant agents based on this ligand's specific metal-ion binding affinity and built-in antioxidant functionalities. Oxidative stress is a recurring theme among neurological disorders including AD, Parkinson's and stroke and will therefore serve as the major focus of the work presented herein as the therapeutic target of 2:

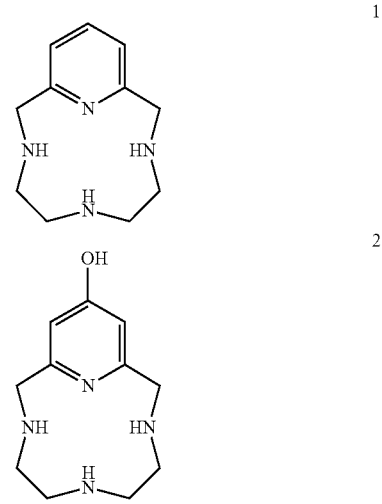

Chart 2

Antioxidant Character.

The in situ capacity of 1 to quench free radicals was first explored using the radical ion DPPH (2,2-diphenyl-1-picrylhydrazyl) and indicated that 1 was an effective antioxidant in the entire 37.5-675 mM range screened. Moreover, a preliminary cell-viability screen of 1 showed a large degree of tolerance in two separate cell lines. Given this success the new congener 2 was produced and showed an enhanced ability to reduce free radicals in solution in the same assay. Compound 2 (Chart 2) exists largely as the pyridol tautomer as confirmed by NMR. The reactivity of pyridol/pyridone based compounds such as chelidamic acid have shown reactivity with OH radicals in solution to form bis-pyridones and is a different mechanism than pyridine based compounds such as 1 (Chart 2). This reactivity is attributed to the enhanced antioxidant capacity observed. Chelidamic acid is the pyridone congener to the starting material used to produce 1. Therefore similar methodologies to produce 2 in gram scale quantities were employed.

Figure 9:
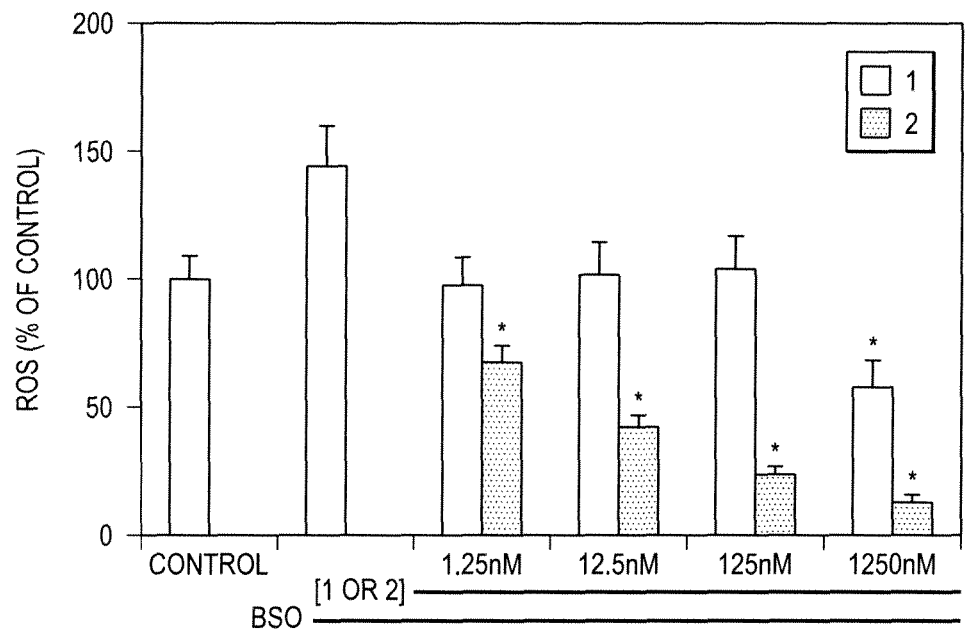
FIG. 9 is a graph of DCFH-DA fluorescent response in FRDA cells after 12 hours exposure to BSO [1 mM] showing dose dependence with 1 and 2.

Cellular studies were carried out to evaluate the intracellular antioxidant efficacy and toxicity of compound 2 (Chart 2) compared to 1 using the cell-permeable fluorophore 2,7'-dichlorodihydrofluorescin diacetate (DCFH-DA) as an indicator for ROS. DCFH-DA diffuses into cells and is deacetylated by cellular esterases to non-fluorescent 2',7'-dichlorodihydrofluorescin (DCFH) which is subsequently oxidized to the highly fluorescent 2',7'-dichlorodihydrofluorescein (DCF) species in the presence of ROS. The fluorescence intensity is directly proportional to the amount of ROS present in cell cytosol.[11] BSO (2-amino-4-(butylsulfonimidoyl)butanoic acid) is a commonly used model for oxidative stress via inhibition of cytosolic glutathione synthesis resulting in elevated intra-cellular [ROS] and an increased fluorescent signal in the presence of DCFH (FIG. 9).

The results of the DCFH-DA cell culture assay indicate that 1 is an effective antioxidant in the 1.25 nM to 1.25 µM range. As shown in FIG. 9 compound 2 is a potent antioxidant at each of the concentrations tested from 1.25 nM to 1.25 µM. While 1 is capable of quenching the ROS induced by BSO, 2 also inhibits the naturally occurring ROS present when compared to the control cells (in growth media only). FIG. 9 shows that at 1.25 nM, 12.5 nM, 125 nM and 1.25 µM [2] there is a decrease of 33%, 58%, 75%, and 87% [ROS] respectively, compared to the untreated cells.

Figure 10:
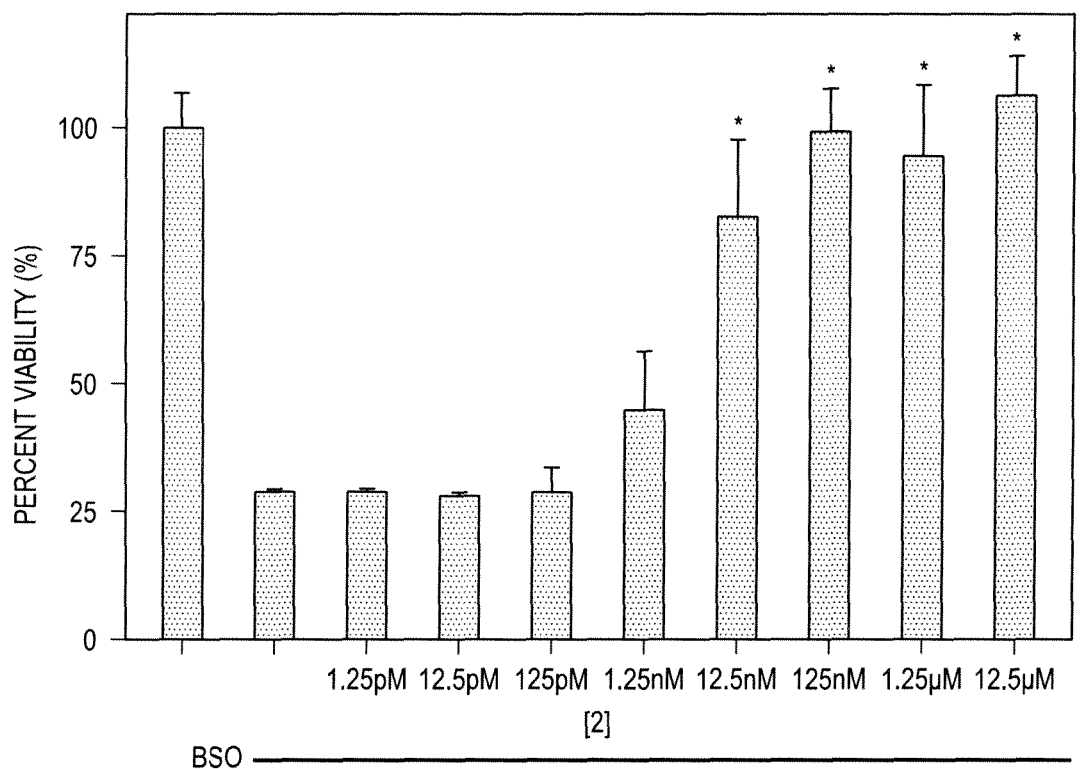
FIG. 10 is a graph showing Calcein AM viability assay of FRDA cells after 48 hour exposure to BSO [1 mM] followed by addition of 2 [various concentrations].
Figure 11:
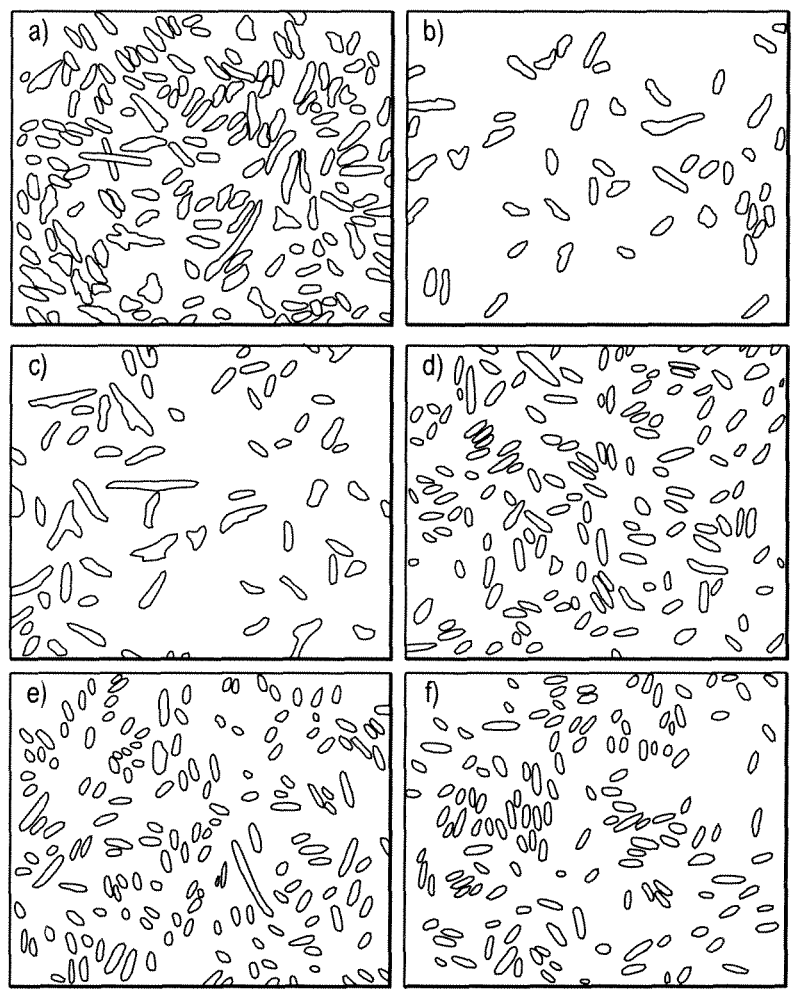
FIG. 11 is an illustration of Fluorescence response of FRDA cells incubated with Calcein AM viability indicator (a) FRDA cells in media only (b) +BSO [1 mM] (c) b+12.5 nM 2 (d) b+125 nM 2 (e) b+1.25 uM 2 (f) b+12.5 uM 2.

Cell viability studies using live-cell penetrating Calcein AM as a fluorophore show that compound 2 (Chart 2) is protective against BSO assault from 1.25 nM to 12.5 µM with an $EC_{50}$ 31.46±4.96 nM (FIG. 10). This dose response is visualized in the fluorescent cell images shown in FIG. 11 with increased cell survival corresponding to increasing 2 in the nM range. As has been mentioned with respect to 1 above, an interesting feature to be noted from these cellular studies is the fact that both 1 and 2 are capable of entering cells and do not appear to interrupt the vital functions of cytosolic metalloenzymes via extraction metal ions from those functionalities.

Beta-Amyloid Prevention/Disaggregation.

Figure 12:
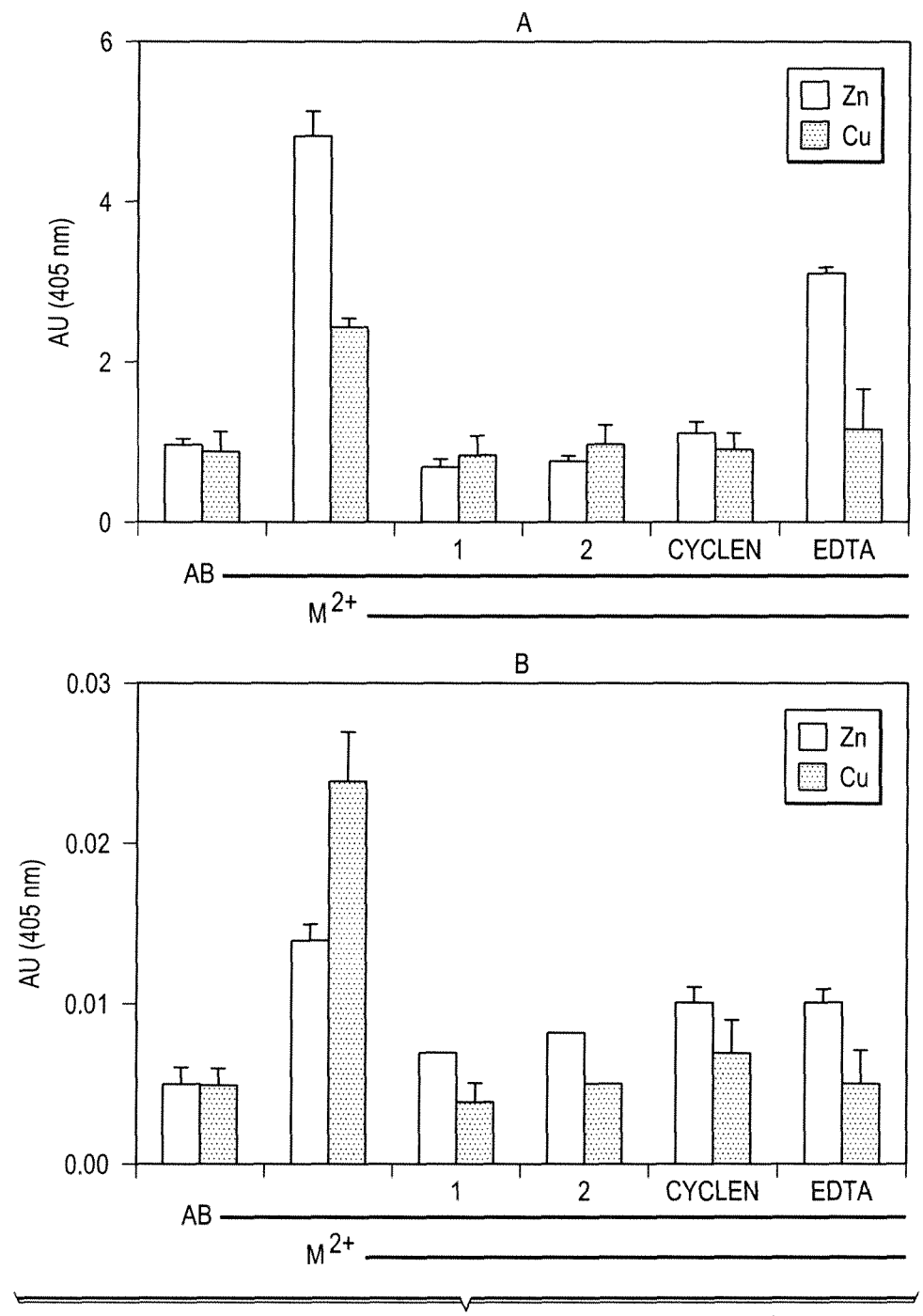
FIG. 12 are Turbidity Assays showing (a) preventative and (b) disaggregative capability of 2 compared to 1, cyclen and EDTA to prevent amyloid plaques.
Figure 13:
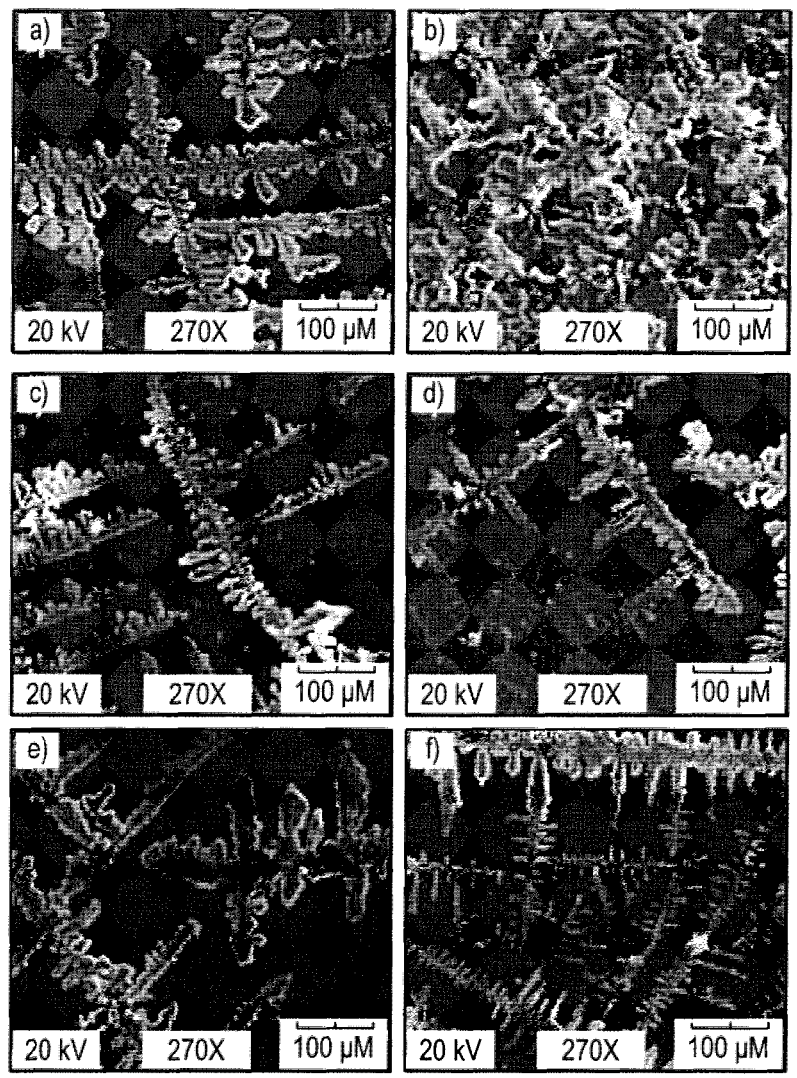
FIG. 13 is a series of SEM Images showing the prevention of amyloid. a) Aβ (b) Aβ+$Cu^{II}$ (c) b+1 (d) b+2 (e) b+cyclen (f) b+EDTA.

The macrocyclic compound 2 (Chart 2) is also a chelator capable of preventing metal-induced amyloid formation as well as disaggregation. Metal ions bind to a histidine rich domain in amyloid producing Aβ in the form of insoluble plaques. This process has been extensively studied and described in a number of recent reviews. As shown in FIG. 12, copper (II) or zinc (II) ion addition to a solution of amyloid$_{1-40}$ results in a turbid solution which scatters light with a consequential increased absorbance signal using absorption spectrophotometry. Turbidity results shown in FIG. 12a show that incubation of 1 or 2 with Aβ$_{1-40}$ prior to addition of $Cu^{II}$ or $Zn^{II}$ prevents formation of aggregations compared to amyloid incubated with metal-ions alone. Moreover, amyloid aggregates formed by metal ion co-incubation can be disaggregated by the addition of compounds 1 or 2 (FIG. 12b). These results were supported using the inherent fluorescence of Tyr$^{10}$ in the Aβ$_{1-40}$ sequence which is quenched upon aggregate formation. Chelators 1 and 2 are equally effective in preventing and re-constituting this signal. These results are compared to macrocyclic and open-chain chelators cyclen and EDTA, and show an equivalent preventative and disaggregative ability with respect to the formation of amyloid plaques.

Part III:

As has been discussed, one therapeutic strategy aimed at abating AD involves the use of metal ion chelator molecules that can decrease the metal accumulation in the brain. These chelator molecules can be categorized into the following general types: chelator antioxidant hybrid molecules, chelator that targets Aβ and metal chelators with enzyme inhibitory activity. This part of Applicant's work concentrates on the chelator antioxidant hybrid molecules.

Design Rational

Metal induced toxicity is often intertwined with the production of reactive oxygen species (ROS) and reactive nitrogen species (RNS) in biological systems. Oxidative stress is a condition in which the production of oxygen radicals increases without a means to neutralize them. By definition, an antioxidant is a substance that prevents the reactions promoted by oxygen, peroxides or free radicals. Generally an antioxidant is able to protect from oxidation via free radical scavenging or by chelating metals conserving the redox equilibrium.

Examples include those by Bebbington and coworkers in which they combine antioxidant terbutylphenols with chelating hydroxypyridones; from the scope they performed with different molecules containing the functional groups mentioned before, the molecule found to exhibit more inhibition of lipid peroxidation as well as ROS protection in rat brain was the combination of BHT (butylhydroxytoluene) with hydroxypyridone shown in Chart 3a below:

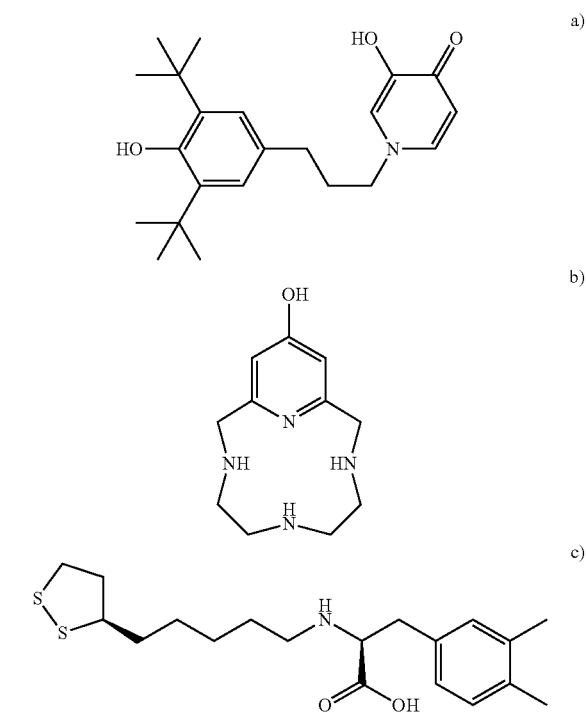

Chart 3a) BHT fused with hydroxypyridone. b) Pyclen backbone hydroxylated. c) Lipoic acid combined to L-DOPA.

Applicants have previously shown that adding hydroxyl groups to well known metal chelating tetraazamacrocycles improves the ability of the molecule to scavenge free radicals compared to pyclen that does not contain the hydroxyl group (Chart 3b). This led Applicants to the synthetic design of compound 1 (Chart 4), whose synthesis will be discussed further in the text.

Chart 4: Hybrid Molecules targeting metal ions and oxidative stress

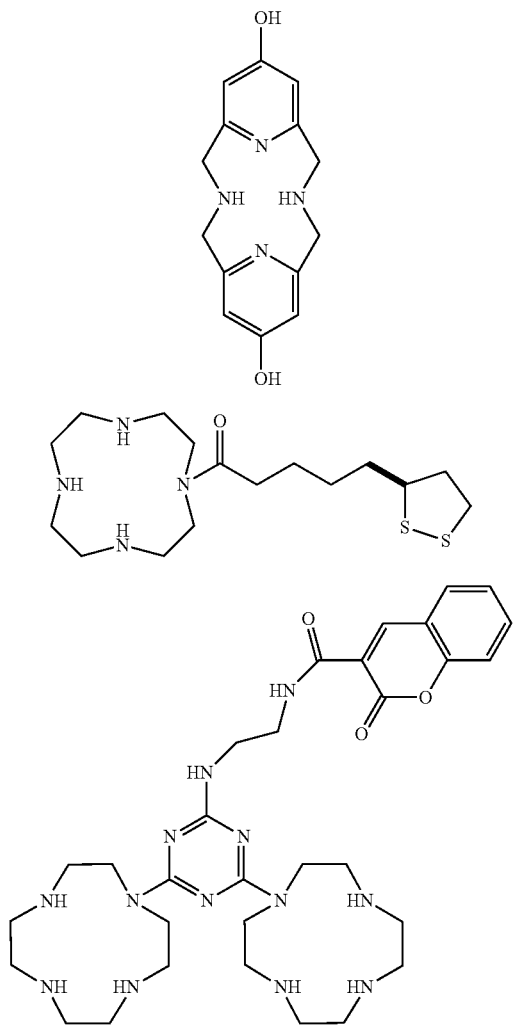

Another interesting strategy was the fusion of L-DOPA with lipoic acid (Chart 3c). L-DOPA is a drug well known for alleviating symptoms of Parkinson's disease, but it presents some disadvantages including poor bioavailability and enzyme degradation as well as generation of ROS catalyzed by the presence of iron or copper. The Di Stefano group circumvented these issues by fusing L-DOPA with α-lipoic acid thus providing an increase in its bioavailability as well as its antioxidant activity.

This later result and the work of others show that lipoic acid is a unique and elegant biological molecule and therefore piqued Applicant's interest for its integration into our library of azamacrocycles (Chart 4, molecule 2). Lipoic acid is already found naturally in both prokaryote and eukaryote organisms as it can act as a coenzyme in metabolic routes of cells.

There have been several in vitro studies proving that α-lipoic acid (LA) and its reduced form dihydrolipoic acid (DHLA) can act as scavengers for reactive oxygen species (ROS) and reactive nitrogen species (RNS) due to a relatively low redox potential (−320 mV). Such studies have also shown cellular protection from ROS generating insults as well as chelation activity of several transition metal species. DHLA is able to restore natural antioxidants such as CoQ (ubiquinol), vitamins C and E and gluthatione. In this Part 3 of the present work, Applicants will focus on the gluthatione restoring pathway since it's the main antioxidant in the brain cells. Glutathione is the lowest molecular weight thiol with major redox potential in animal cells, and whose cellular concentration is markedly decreased by protein malfunctioning, oxidative stress amongst other pathologies. Considering all of these roles it is clear that GSH is important in regulating oxidation processes, thus administration of antioxidants like LA in cases of pathologies involved with oxidative stress is crucial; For example when LA is orally administered it is promptly reduced to DHLA ($pK_a$=4.7) which has been shown to be the active form for radical scavenging. Finally another aspect to consider, since our target protein resides inside the brain, is that LA readily crosses the blood brain barrier.[10] Compared with other disulfide containing molecules LA and DHLA can cross mitochondria and cell membranes without difficulty, making these molecules very suitable for modulating gluthatione levels.

Aside from these properties lipoic acid is also well known for its capacity to chelate transition metals, which is an additional reason for choosing this as a scaffold in our synthetic design. Studies performed by Suh and coworkers have demonstrated that DHLA and LA bind strongly to copper ions but only DHLA inactivates metal ions redox activity (Chart 5). Both species are capable of lowering ascorbate oxidation but neither interfere with the aconitase or SOD inherent metals. Considering the labile nature of the iron in the aconitase enzyme, it is a good example to show that LA and DHLA will not interfere with the metal activity of these enzymes. In other words evidence to date suggests that DHLA and LA do not remove metals form the metalloprotein active sites.

CHART 5

1) $O_2^{\bullet-} + Fe(III) \rightarrow O_2 + Fe(II)$
2) $2O_2^{\bullet-} + 2H^+ \rightarrow O_2 + H_2O_2$
3) $Fe(II) + H_2O_2 \rightarrow Fe(III) + OH^- + HO^{\bullet}$ Chemistry of iron or copper mediated free radical production and toxicity. Haber-Weiss reaction. 1)
Reduction of iron by $O_2^{\bullet-}$ that reacts with $H_2O_2$ by dismutation of $O_2^{\bullet-}$ 2)
Finally $HO^{\bullet}$ radicals are generated by Fenton reaction 3)

Another interesting set of molecules possessing antioxidant activity are coumarins; in vitro studies have shown that coumarins also have the ability to quench hydroxyl radicals and superoxide radicals. Plus, these molecules can inhibit lipid peroxidation in addition to acting as a vasorelaxant, antiinflamatory and anticoagulant.

According to Manevich and coworkers, a derivative of coumarin, coumarin-3-carboxylic acid, reacts with reactive oxygen species, resulting in hydroxylation in positions 5 and 7 mostly, and generating a fluorescent compound. We postulate that molecule 3 (Chart 4) will take advantage of those properties conserving the cyclen scaffold, with the fusion of the two chelating cyclen cores, in addition to the properties engendered by coumarin-3-carboxylic acid. When the latter reacts with ROS residing in the brain, compound 3 (Chart 4) is designed to not only to quench free radicals by previously mentioned methods, but its hope to allow one to track it across the cell thanks to its fluorescent signal.

Results and Discussion

Synthesis of compounds 1-3 (Chart 4): The chelator hybrid molecules proposed herein, involve the substitution of the 1,4,7,10-tetraazacyclododecane (cyclen) retaining its chelating capabilities as well as enhancing the ligand construct with an antioxidant moiety. Our first target is compound 1 in Chart 4 (2-PC). Synthesis (detailed in SI) starts with the esterification of chelidamic acid with thionyl chloride and ethanol, followed by the protection of the hydroxyl group by the Williamson ether synthesis. The next step involves the reduction of the ester to an alcohol followed by the formation of the alkyl halide to create the azamacrocycle with the tosylamide salt in DMF. Finally, naphthalene catalyzed reductive deprotection of both the benzyl group and the tosylsulfonamides groups.

The synthesis of compound 2 (LC in Chart 4) begins with the protection of 1,7-amines of cyclen with benzyl chloroformate. Concurrently, conversion of lipoic acid to lipoic chloride with thionyl chloride in dichloromethane proceeded smoothly in quantitative yield. These two products react in the presence of triethylamine to form an amide bond in position 10 of cyclen through a nucleophilic substitution at the carbonyl group; bisubstitution of cyclen with lipoic chloride is observed with very low yield in the reaction and can be separated using column chromatography. Finally, deprotection of the Cbz group with boron trichloride gave the desired product.

The last synthesis presented in this report is compound 3 (C.C in Chart 4), and starts with the protection of cyclen, using terbutyldicarbamate (Boc) in 1,4,7 positions followed by a nucleophilic substitution of cyanuric chloride with two molecules of the protected cyclen. A third nucleophilic substitution of the triazine like core with ethylenediamine is then carried out, followed by a condensation reaction with coumarin-3-carboxylic acid. Finally deprotection of the Boc groups with HCl/dioxane yields the desired product.

Radical Quenching Assay

Figure 14:
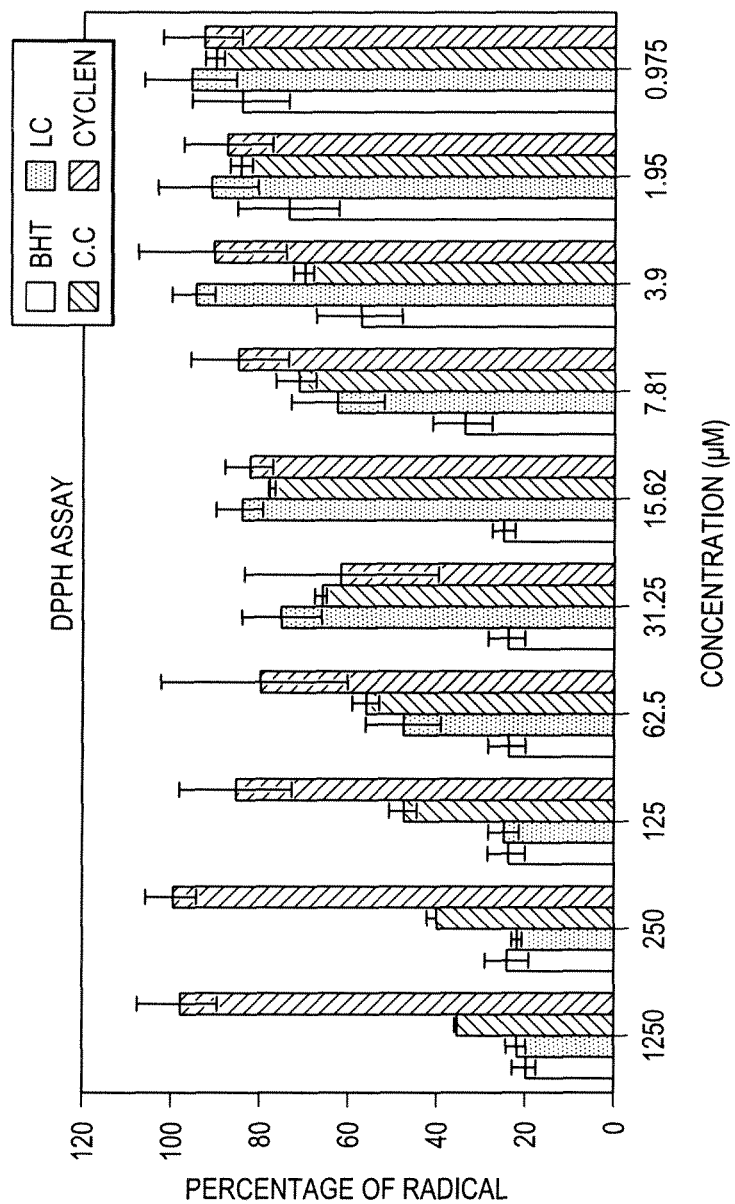
FIG. 14 is an illustration which shows graphically that at high concentrations (1250 µM) BHT is capable of quenching 80% of the DPPH radical while cyclen shows no activity.

As radicals are one product of miscompartmentalized metal ions, radical scavenging capability of compounds 1-3 (Chart 4) was tested using the DPPH assay. DPPH (2,2-diphenyl-1-picrylhydrazyl), is a dark purple ($\lambda_{max}$=540 nm), stable free radical in solution that can be reduced to DPPHH in the presence of molecules with radical scavenging activity. This process results in a color change from dark purple to light yellow and can be followed spectroscopically by the decrease of the band at 540 nm. Applicants have, therefore, utilized this method to measure radical scavenging capability of their own organic molecules. BHT (butylhydroxytoluene) was used as a positive control due to its known antioxidant properties. FIG. 14 shows that at high concentrations (1250 μM) BHT is capable of quenching 80% of the DPPH radical while cyclen shows no activity. Compound 2 (Chart 4) under the same conditions its proficient at quenching an equivalent amount of radical, following a dose response trend up to 62.5 μM concentration. If we compare these results to compound 2 (LC) with the original backbone, cyclen, we can see that between 1250 μM and 62.5 μM radical scavenging activity of the latter is improved.

Finally, it is observed that compound 3 (Chart 4) quenches 52-64% of the DPPH radical showing that integration of a cumarin scaffold onto the cyclen backbond also results in an increase of radical scavenging capacity. These results lead us to the inclusion of antioxidant moieties combined with the cyclen core result in ability for quenching free radicals with a concentration dependent response.

Toxicity in Cells

Figure 15:
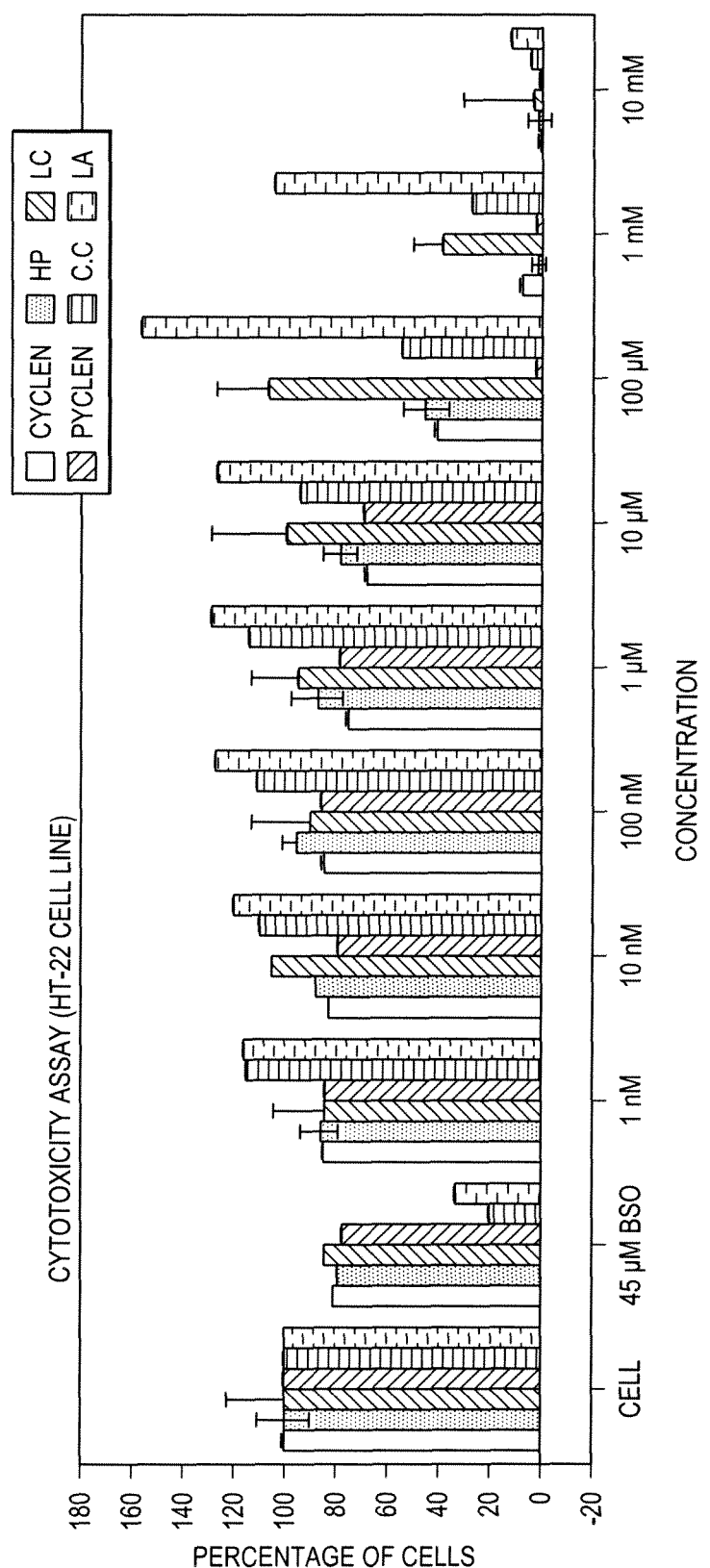
FIG. 15 is a graph of a cytotoxicity assay plotting percentage of cells versus concentration indicating that at 100 µM concentration there should still be antioxidant activity in cells, without increasing cell death due to the compound.

As these compounds show potential for future in vivo studies, the 3-(4,5-dimethythiazol-2-yl)-2,5-diphenyl tetrazolium bromide (MTT) assay was performed in order to test compounds 2, 3 of Chart 4 for cytotoxicity with HT-22 cells, which is a hippocampal neuronal cell line extracted from mice. This is a colorimetric assay that measures the mitochondrial activity of living cells in which MTT crosses into the mitochondria where it is reduced to media insoluble formazan (dark purple), which is later solubilized in DMSO and measured spectroscopically ($\lambda_{max}$=540 nm). Since the reduction of MTT can only occur in living cells with undamaged mitochondria, this is a good assay to measure cell proliferation and cytotoxicity. Information in FIG. 15 was used to calculate the $EC_{50}$ of compound 2 (312.3 μM) which correlates nicely with the DPPH assay, indicating that at the 100 μM concentration one should still have antioxidant activity in cells, without increasing cell death due to compound. Same for compound 3 where the $EC_{50}$ value is 125 μM.

Toxicity of Aβ and $Cu^{+2}$

Figure 16:
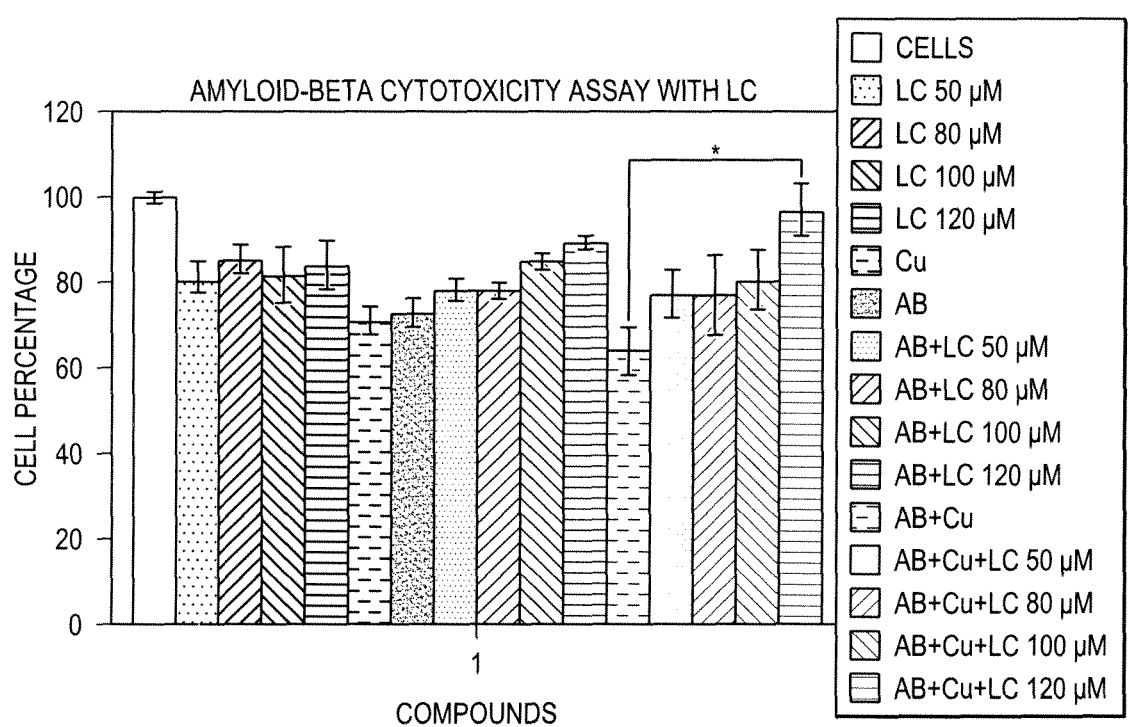
FIG. 16 is a graph of an amyloid-beta cytotoxicity assay showing that compound 2 (LC) is capable of protection in ranges from 50 to 120 µM.

Once the toxicity of compounds 2 and 3 (Chart 4) was established, Aβ tests were made to support the hypothesis of an increase in toxicity of amyloid upon addition of $Cu^{+2}$ and to show that compounds 2 and 3 are capable of protecting against that toxicity. In FIG. 16 one can observe that compound 2 (LC) is capable of protection from ranges of 50 to 120 μM reaching 37% of increase of cell proliferation with respect to the control (Aβ+$Cu^{+2}$). It is also shown that Aβ toxicity (15 μM) increases upon addition of copper (15 μM) opening the possibility of explaining the mechanism of action of LC (compound 2) which involves the possible chelation of copper out of the plaques, although the possibility of assessing ROS is always present. The experiment is completed with several controls including just compound 2, (Chart 4) and just copper, for comparison purposes.

The same analysis was performed for compound 3, (Chart 4), keeping the same ranges of concentrations for the compound (50 to 120 μM) as well as amyloid and copper. Restoring of cell proliferation was observed from 3 to 17%.

Experimental Protocol for the Synthesis of Part 3 Compounds:

General.—

All reagents used were obtained from commercial sources and used as received, unless noted otherwise.

$^1$H NMR spectra were obtained on a 300-MHz Varian Gemini 2000 spectrometer, using deuterated solvents (CDCl$_3$, D$_2$O, DMSO) with tetramethylsilane as internal reference (in parts per million) (Me$_4$Si, δ=0.00 ppm). $^{13}$C NMR spectra were obtained at 75-MHz using CDCl$_3$ as internal reference (δ=77.36 ppm).

For proper identification of the NMR signals the following abbreviations were used: s=singlet, d=doublet, t=triplet, m=multiplet.

When noted purification of the compounds was accomplished with flash chromatography using silica gel (63-200 μm), TLC plates developed using iodine, UV light, or staining the plates with a phosphomolybdic acid solution (10 wt. % of phosphomolybdic acid in ethanol) followed by heating.

DPPH Assay.—

DPPH stock solution was prepared by dissolving 25 mg in 100 mL of absolute EtOH. The working radical solution was prepared by dilution with absolute EtOH to an absorbance of 1.3 at 512 nm. Stock solutions of the compounds tested were dissolved in DI H$_2$O and EtOH 95% respectively and serial dilutions were made to get different concentrations. For the analysis 2 mL of the solutions were incubated with 2 mL of DPPH working solutions in the dark for 24 h. as well as 2 mL of DPPH working solution with 2 mL of H$_2$O or EtOH to serve as blank. Analysis of the solutions was performed as follows: 1 mL of the sample solution was diluted with 1 mL of H$_2$O shaken and the absorbance was measured at 515 nm.

Biological Methods.—

For the biological assays mouse hippocampal HT-22 cell line was used, incubated them at 37° C. in a humidified atmosphere 5% $CO_2$, with Dulbecco's Modified Eagle Medium (500 ml) containing penicillin/streptomycin 100× (5 ml), Glutamine (100 mM, 5 ml), charcoal strip fetal bovine serum. To prepare samples containing compounds the same media was used excluding the addition of the serum.

MTT Assay.—

(3-(4,5-dimethylthiazol-2-yl)-2,5-diphenyltetrazolium bromide) cells were seeded in a 96 well plate with a density of 5000 cells per well (in 100 μL per well). After 24 h. cells were treated with compounds, Aβ, $Cu^{+2}$, or a combination of these depending on the case, and incubated for 48 h. at 37° C. After the incubation media was discarded and cells were then treated with 100 μL of MTT (1 mg/1 mL in media) and incubated for 4 h at 37° C. Media is discarded again and 100 μL of DMSO are added to each well, rocked for 5 minutes and the absorbance ($A_{510}$) was measured using a Molecular Devices Kinetic Microplate Reader.

Synthesis of (1)

Step 1.—Preparation of Diethyl-4Hydroxypyridine-2,6-dicarboxylate (4)

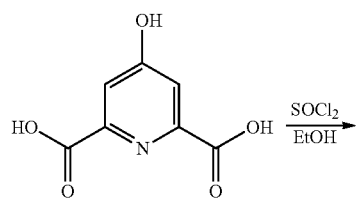

To a mixture of EtOH (200 mL) and $SOCl_2$ (7.9 mL, 108 mmol) in an ice bath and under nitrogen, chelidamic acid (7.9 g, 43 mmol) was added and the mixture was refluxed at 70° C. for 5 h. The solvent was rotovaped in vacuum and the residue was washed with toluene and evaporated (3×). The residue was suspended in diethylether and water, mixed it, to get the product precipitating as white crystals, then filtered and dried under vacuum to yield 98% of the product as a white solid.

$^1$H NMR (300 MHz, $CDCl_3$): δ[ppm]=1.3 (t, $CH_2CH_3$, 6H), 4.3 (q, $CH_2CH_3$, 4H), 7.4 (s, py H, 2H), 9.2 (s, OH, 1H); $^{13}$C NMR (75 MHz, $CDCl_3$): δ[ppm]=14.2, 18.3, 58.3, 63.0, 118.0, 163.5.

Step 2.—Preparation of Diethyl 4-(Benzyloxy)pyridine-2,6-dicarboxylate (5)

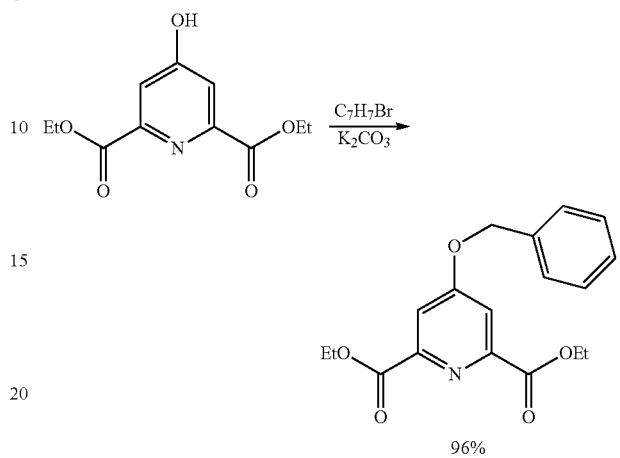

To a solution of 4 (6.88 g, 28 mmol) in acetonitrile and $K_2CO_3$ (6.31 g, 45 mmol) was carefully added benzyl bromide (3.34 mL, 27 mmol). The resulting solution was stirred at 82° C. under reflux overnight. The reaction was stopped by filtration of $K_2CO_3$ and the solvent was removed under reduced pressure. The solid obtained was recrystallized from hot hexanes to yield 96% of the product as a white solid.

$^1$H NMR (300 MHz, $CDCl_3$): δ[ppm]=1.4 (t, $CH_2CH_3$, 6H), 4.4 (q, $CH_2CH_3$, 4H), 5.2 (s, $CH_2Bz$, 2H), 7.3 (m, Ar H, 5H), 7.8 (s, py H, 2H); $^{13}$C NMR (75 MHz, $CDCl_3$): δ[ppm]= 14.1, 62.4, 70.7, 114.6, 127.7, 128.7, 128.8, 135.0, 150.0, 164.8, and 166.6.

Step 3.—Preparation of 4-(Benzyloxy)-2,6-bis(hydroxymethyl)pyridine (6)

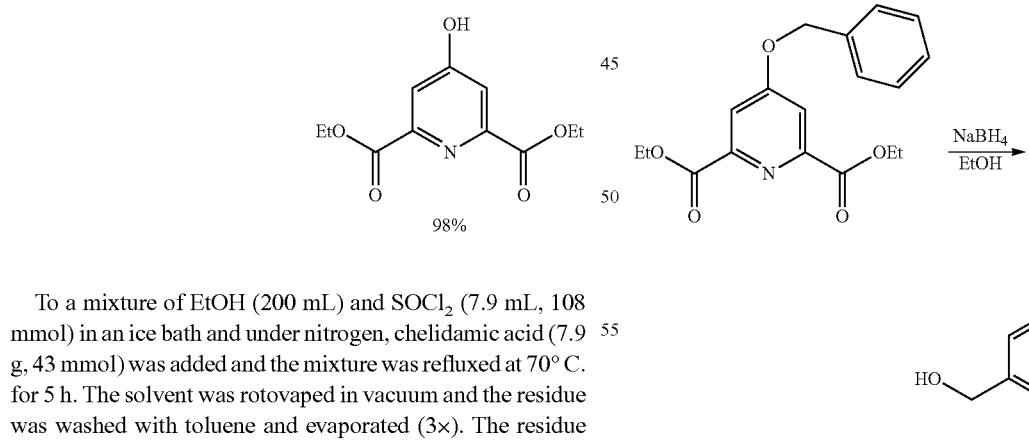

Over a solution of 5 (3.8 g, 11 mmol) in anhydrous EtOH, $NaBH_4$ was carefully added (2.61 g, 68 mmol). The resulting solution was stirred at 40° C. for 24 h. then the reaction was quenched with $H_2O$. EtOH was rotovaped down half the total volume, extracted with EtOAc (5×) dried with $NaSO_4$ and the solvent was evaporated to obtain 90% of a white solid as the product.

$^1$H NMR (300 MHz, DMSO): δ[ppm]=4.4 (s, CH$_2$OH, 4H), 5.1 (s, CH$_2$OH, 2H), 5.3 (s, CH$_2$C$_6$H$_5$, 2H), 6.9 (s, py H, 2H), 7.3 (m, Ar H, 5H); $^{13}$C NMR (75 MHz, DMSO): δ[ppm]=62.6, 67.6, 103.3, 126.3, 126.7, 127.1, 135.0, 161.7, 164.4.

Step 4.—Preparation of 4-Benzyloxy-2,6-bis(chloromethyl)pyridine (7)

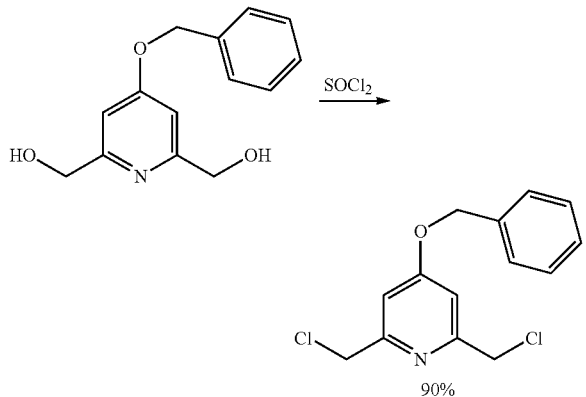

Thionyl chloride (22 mL, 234 mmol) was added slowly to 6, the clear solution was heated under reflux at 60° C. for 4 h. The solution was then allowed to cool down to room temperature and excess of thionyl chloride was removed under reduced pressure. The residue was neutralized with a cold solution of 10% NaCO$_3$. The resultant precipitate was filtered and thoroughly washed with cold H$_2$O. The white solid obtained was further recrystallized with MeOH to yield white needle shaped crystals 90%.

$^1$H NMR (300 MHz, CDCl$_3$): δ[ppm]=6.6 (s, CH$_2$Cl, 4H), 5.1 (s, CH$_2$C$_6$H$_5$, 2H), 7.0 (s, py H, 2H), 7.4 (m, Ar H, 5H); $^{13}$C NMR (75 MHz, CDCl$_3$): δ[ppm]=46.7, 70.4, 109.0, 127.9, 128.8, 129.0, 135.8, 158.2, 168.3.

Step 5.—Preparation of the N-Tosyl Azamacrocycle (8)

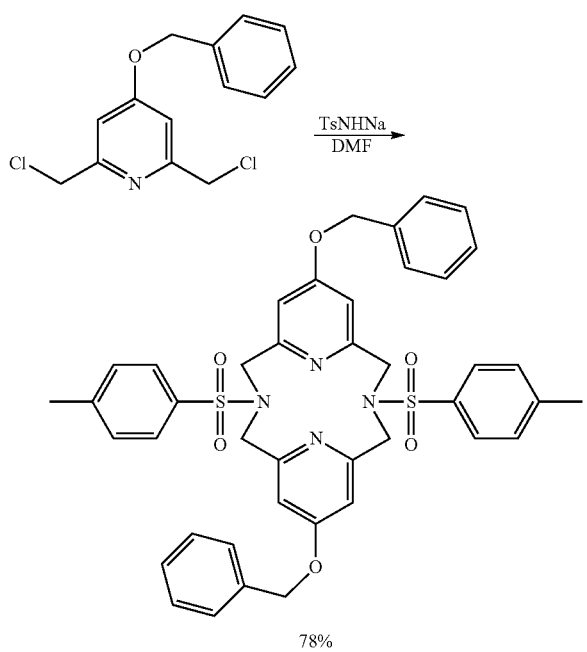

To a stirred solution of TsNHNa (698 mg, 4 mmol) in anhydrous DMF at 80° C. was added dropwise under a N$_2$ atmosphere a solution of 7 (1 g, 2 mmol) in DMF. After 1 h. solid TSNHNa (698 mg, 4 mmol) was added at once, and the mixture was stirred at 80° C. for 4 h. On cooling, product precipitates out of the reaction mixture overnight with the evaporation of most of the solvent. Product was crystallized with MeOH to yield 78% as white powder; No NMR data was obtained due to limited solubility of the compound but a crystal structure was obtained instead.

Step 6.—Preparation of (1)

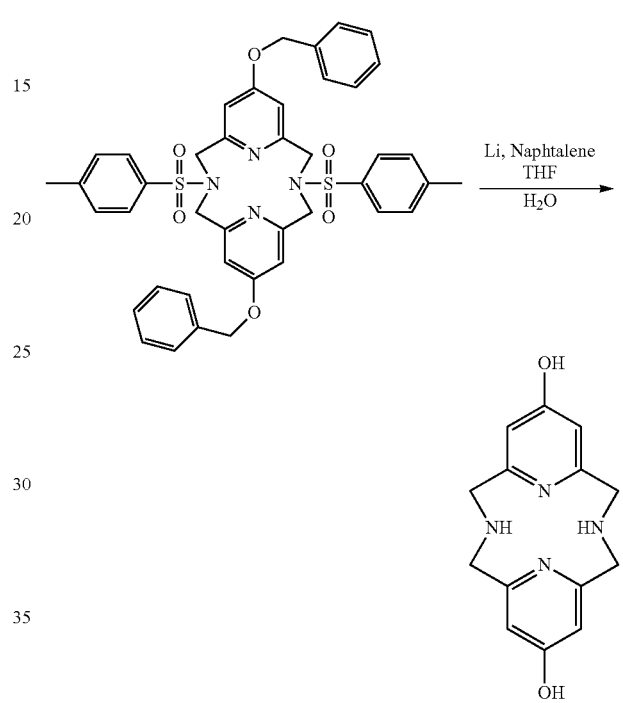

To a green suspension of lithium and naphthalene in THF was slowly added a solution of 8 in THF at –78° C. and stirred overnight. The resulting mixture was hydrolyzed with H$_2$O and extracted with Et$_2$O and the neutralized with HCl$^6$. Liophilized and recrystallized with MeOH and ether to yield the product as beige solid.

H NMR (300 MHz, D$_2$O): δ[ppm]=4.2 (s, CH$_2$—NH, 8H), 6.4 (s, CH-phenyl, 4H); $^{13}$C NMR (75 MHz, D$_2$O): δ[ppm]=51.9, 111.7, 151.0, 165.6; MS (ESI, CH$_3$CN:H$_2$O+ 0.1% CH$_2$O$_2$) m/z=273 [+H].

Synthesis of (±)-5-(1,2-dithiolan-3-yl)-1-(1,4,7,10-tetraazacyclododecan-1-yl)pentan-1-one (LC) (2)

Step 1.—Preparation of (±)-5-(1,2-dithiolan-3-yl) pentanoyl chloride (9)

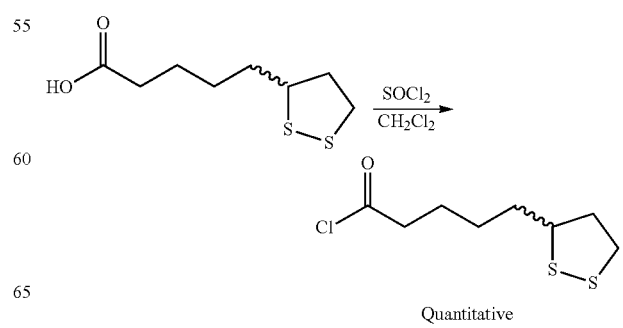

To a stirred solution of thionyl chloride (1.4 mL, 7.5 mmol) in CH$_2$Cl$_2$ (30 ml) at 0° C. was added a solution of lipoic acid (3.0 g, 5 mmol), dissolved in dichloromethane, dropwise over 1 h. The mixture was allowed to stir for additional 3 h. at the same temperature. After completion of the reaction the solvent was removed under vacuum using a dry-ice collection trap being very careful not to heat the reaction mixture since this will decompose the product. Reaction proceeds with quantitative yield.

H NMR (300 MHz, CDCl$_3$): δ[ppm]=1.6 (m, 2H, CH$_2$C), 1.8-1.9 (m, 2H, CH$_2$CHS), 2.4-2.5 (m, 2H, CH$_2$CO, 2.8-2.9 (t, 2H, CH$_2$S), 3.5 (q, 1H, CHS).

Step 2.—Preparation of dibenzyl 1,4,7,10-tetraazacyclododecane-1,7 dicarboxylate (10)

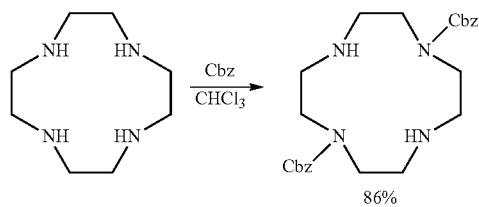

Compound 10 was produced according to Sherry et. al. method. Benzyl chloroformate (Cbz) (7.1 mL, 2 mmol) was added dropwise to a solution of cyclen in CHCl$_3$ (3.0 g, 1.02 mmol) previously cooled in an ice bath. The solution was allowed to warm to room temperature and stirred overnight. The volume of the solution was then reduced by half and Et$_2$O was used to precipitate a white solid that was collected via filtration. The solid was resuspended in H$_2$O and a concentrated aqueous solution of NaOH was added. Et$_2$O was used to extract the product from the basic water layer. The organic phase was washed twice with DI H$_2$O, dried over Na$_2$SO$_4$, filtered and rotovaped down, to yield 86%.

H NMR (300 MHz, CDCl$_3$): δ[ppm]=2.6-2.8 (broad, 16H, CH$_2$CH$_2$), 5.1 (s, 4H, CH$_2$Ph), 7.3 (m, 10H, Ph); $^{13}$C NMR (75 MHz, CDCl$_3$): δ[ppm]=48.5, 48.7, 49.4, 49.8, 50.4, 50.9, 51.1, 51.3 (CH$_2$-cyclen), 67.3 (CH$_2$-benzyl), 128.0, 128.1, 128.2, 128.2, 128.7 (CH-phenyl), 136.8 (CH-phenyl), 157.0 (C=O).

Step 3.—Preparation of the (±)-dibenzyl 4-(5-(1,2-dithiolan-3-yl)pentanoyl)-1,4,7,10-tetraazacyclododecane-1,7-dicarboxylate (11)

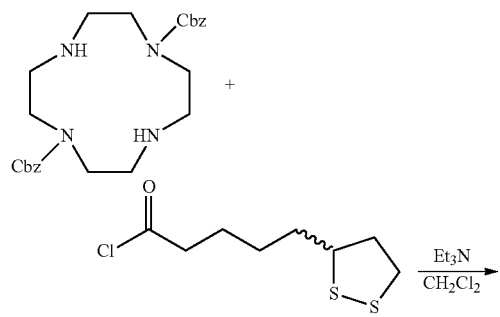

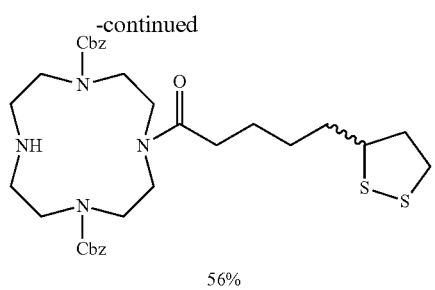

56%

To an iced bath cooled solution of 10 (5.8 g, 5.7 mmol) and triethylamine (5.6 mL, 40.1 mmol) in CH$_2$Cl$_2$ was continuously added the prepared solution of 9 (3.0 g, 13.3 mmol) in CH$_2$Cl$_2$ dropwise. The reaction mixture was stirred in an ice bath overnight. The mixture was washed with a saturated solution of sodium bicarbonate, 1N HCl, brine and dried over Na$_2$SO$_4$, filtrate, and the solvent was then removed under reduced pressure, the crude product was purified by column chromatography 5% MeOH:EtOAc, obtaining a yellow oil 56% isolated yield.

$^1$H NMR (300 MHz, CDCl$_3$): δ[ppm]=1.5 (m, 2H, CH$_2$C), 1.6 (m, 2H, CH$_2$CHS), 2.3-2.5 (t, 2H, CH$_2$S), 2.8-2.9 (broad, 12H, CH$_2$CH$_2$), 3.1-3.5 (m, 2H, CH$_2$CO), 3.5-3.6 (q, 1H, CHS), 5.0 (s, 4H, CH$_2$Ph), 7.3 (m, 10H, Ph); $^{13}$C NMR (75 MHz, CDCl$_3$): δ[ppm]=24.6, 29.0, 31.9, 34.8 (CH$_2$—CH$_2$-alkyl), 38.4 (CH$_2$CH$_2$S), 40.2 (CH$_2$S), 46.2, 47.7, 48.1, 48.5, 49.8, 50.5, 50.7, 51.7 (CH$_2$-cyclen), 56.5 (CHS), 66.9, 67.0, 67.1, 67.6 (CH$_2$-benzyl), 127.7, 127.8, 128.0, 128.3, 128.4, 128.5, 128.6 (CH-phenyl), 136.5 (CH-phenyl), 156.2, 156.4 (C=O), 172.3, 172.6 (N—C=O); MS (ESI, CH$_3$CN:H$_2$O+ 0.1% CH$_2$O$_2$) m/z=629 [+H]

Step 4.—Preparation of (±)-5-(1,2-dithiolan-3-yl)-1-(1,4,7,10-tetraazacyclododecan-1-yl)pentan-1-one (12)

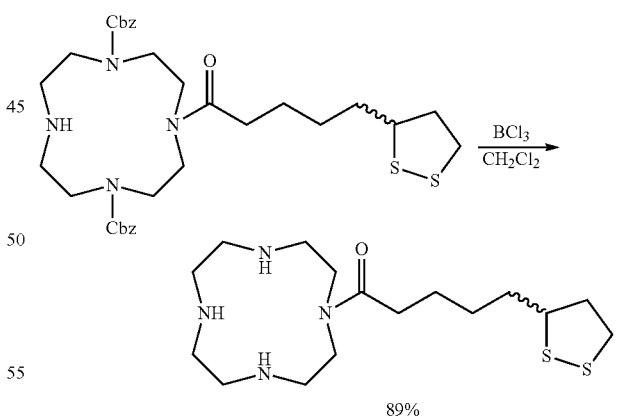

89%

Boron trichloride in CH$_2$Cl$_2$ (1 mL, 8.5 mmol) was carefully added to a previously purged flask with nitrogen, containing 11 (1.2 g, 1.9 mmol). The white suspension was then allowed to stir for 3 h. Excess CH$_2$Cl$_2$ was removed under reduced pressure. To the resultant yellow solid was added MeOH and rotavaped down (2×). HCl was added to the residue, and the aqueous layer washed with EtOAc, neutralized and lyophilized to yield the product as a yellow solid 89% yield.

H NMR (300 MHz, CDCl$_3$): δ[ppm]=1.5 (m, 2H, CH$_2$C), 1.6 (m, 2H, CH$_2$CHS), 2.3-2.5 (t, 2H, CH$_2$S), 2.8-2.9 (broad, 12H, CH$_2$CH$_2$), 3.1-3.5 (m, 2H, CH$_2$CO), 3.5-3.6 (q, 1H, CHS), 5.0 (s, 4H, CH$_2$Ph); $^{13}$C NMR (75 MHz, CDCl$_3$): δ[ppm]=24.6, 29.0, 31.9, 34.8 (CH$_2$—CH$_2$-alkyl), 38.4 (CH$_2$CH$_2$S), 40.2 (CH$_2$S), 46.2, 47.7, 48.1, 48.5, 49.8, 50.5, 50.7, 51.7 (CH$_2$-cyclen), 56.5 (CHS), 156.2, 156.4 (C=O), 172.3, 172.6 (N—C=O); MS (ESI, CH$_3$CN:H$_2$O+0.1% CH$_2$O$_2$) m/z=321 [+H]

Step 4.—Copper complex of (±)-5-(1,2-dithiolan-3-yl)-1-(1,4,7,10-tetraazacyclododecan-1-yl)pentan-1-one (13)

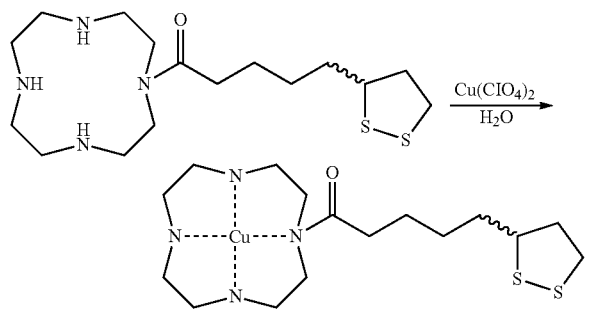

Ligand 12 (50 mg, 0.1 mmol) was dissolved in 5 mL of H$_2$O, adjusted pH=6 using NaOH. A solution of Cu(ClO$_4$) (51.1 mg) dissolved in H$_2$O (about 1 mL) was added dropwise over 10 minutes. The solution was stirred overnight to ensure formation of the complex.

MS (ESI, CH$_3$CN:H$_2$O+0.1% CH$_2$O$_2$) m/z=423.

Synthesis of N-(2-((4,6-di(1,4,7,10-tetraazacyclododecan-1-yl)-1,3,5-triazin-2-yl)amino)ethyl)-2-oxo-2H-chromene-3-carboxamide (3)

Step 1.—Preparation of 1,4,7-tristertbutoxycarbonyl 1,4,7,10 tetraazacyclododecane (14)

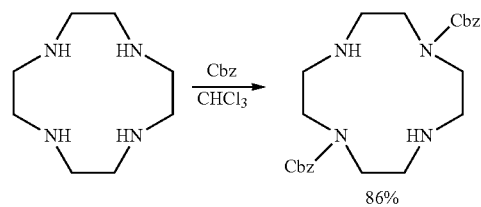

A solution of Tertbutyldicarbamate (Boc) 11.5 g, 52.6 mmol) in CHCl$_3$ was added dropwise to a solution of cyclen (3.0 g, 17.4 mmol) and triethylamine (7.3 mL, 52.6 mmol) in CHCl$_3$ while cooled in an ice bath. The solution was warmed to room temperature and stirred overnight, then the reaction mixture was washed with water, the organic layer was dried over Na$_2$SO$_4$, filtered and solvent removed under reduced pressure. Silica column chromatography 5% MeOH:CH$_2$Cl$_2$ provided pure compound, 82% yield.

H NMR (300 MHz, CDCl$_3$): δ[ppm]=1.3 (s, 18H, C(CH$_3$)$_3$), 1.4 (s, 9H, C(CH$_3$)$_3$), 2.8 (broad, 4H, ring CH$_2$), 3.2 (broad, 8H, ring CH$_2$), 3.5 (broad, 4H, ring CH$_2$); $^{13}$C NMR (75 MHz, CDCl$_3$): δ[ppm]=28.6, 28.8 (((C(CH$_3$)$_3$), 46.1, 49.6, 50.6, 51.2, (ring CH$_2$), 79.3, 80.1 (((C(CH$_3$)$_3$), 155.8 (C=O).

Step 2.—Preparation of 4 Chloro-2,6-bis(1,4,7,10-tetraazacyclododecane-4,7,10-tricarboxylic acid tritert-butylester-1-yl)-[1,3,5]-triazine (15)

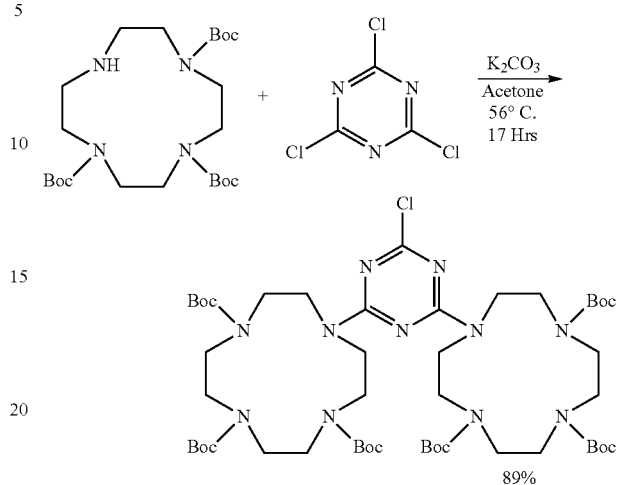

Cyanuric chloride (300.0 mg, 0.16 mmol) was placed in a round bottom flask with K$_2$CO$_3$ (470.0 mg, 3.4 mmol) suspended in acetone. To this suspension 14 (1.7 g, 3.5 mmol) was added dropwise; the reaction mixture is heated under reflux for 17 h., followed by filtration and excess of acetone is removed under reduced pressure, to yield 89% of product.

H NMR (300 MHz, CDCl$_3$): δ[ppm]=1.4-1.5 (s, 54H, CH$_3$-Boc), 3.3-3.6 (broad, 32H, CH$_2$-cyclen); $^{13}$C NMR (75 MHz, CDCl$_3$): δ[ppm]=28.63, 28.67 (CH$_3$-Boc), 50.0 (broad, CH$_2$-cyclen), 80.4 (C$_{quat}$, C-Boc), 156.5 (C$_{quat}$, C=O-Boc), 165.2 (C$_{quat}$, triazine-C$_{aryl}$—N), 169.2 (C$_{quat}$, triazine-C$_{aryl}$—Cl); MS (ESI, CH$_3$CN:H$_2$O+0.1% CH$_2$O$_2$) m/z=1056 [+H]

Preparation of hexa-tert-butyl 10,10'-(6-((2-aminoethyl)amino)-1,3,5-triazine-2,4-diyl)bis(1,4,7,10-tetraazacyclododecane-1,4,7-tricarboxylate) (16)

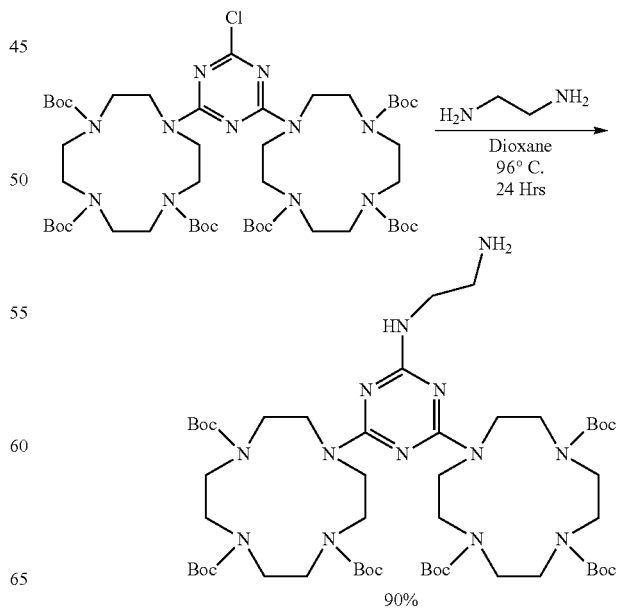

To a solution of 15 (2.4 g, 2.2 mmol) in dioxane was added ethylenediamine (0.44 mL, 7.3 mmol) and heated under reflux for 24 h., solvent was rotavaped and the residue was washed with water and ethyl acetate. Product was used in the next reaction without further purification, with 90% yield.

H NMR (300 MHz, CDCl$_3$): δ[ppm]=1.4 (s, 54H, CH$_3$-Boc), 2.8 (s, 4H, CH$_2$CH$_2$), 3.2-3.7 (broad, 32H, CH$_2$-cyclen), 5.1 (s, 4H, NH$_2$); $^{13}$C NMR (75 MHz, CDCl$_3$): δ[ppm]=28.6, 28.7, 28.9 (CH$_3$-Boc), 42.2 (CH$_2$CH$_2$) 50.5 (broad, CH$_2$-cyclen), 79.9 ($C_{quat}$, C-Boc), 156.5 ($C_{quat}$, C=O-Boc), 166.2 ($C_{quat}$, triazine-$C_{aryl}$—N); MS (ESI, CH$_3$CN:H$_2$O+0.1% CH$_2$O$_2$) m/z=1080 [+H]

Preparation of hexa-tert-butyl 10,10'-(6-((2-(2-oxo-2H-chromene-3-carboxamido)ethyl)amino)-1,3,5-triazine-2,4-diyl)bis(1,4,7,10-tetraazacyclododecane-1,4,7-tricarboxylate) (17)

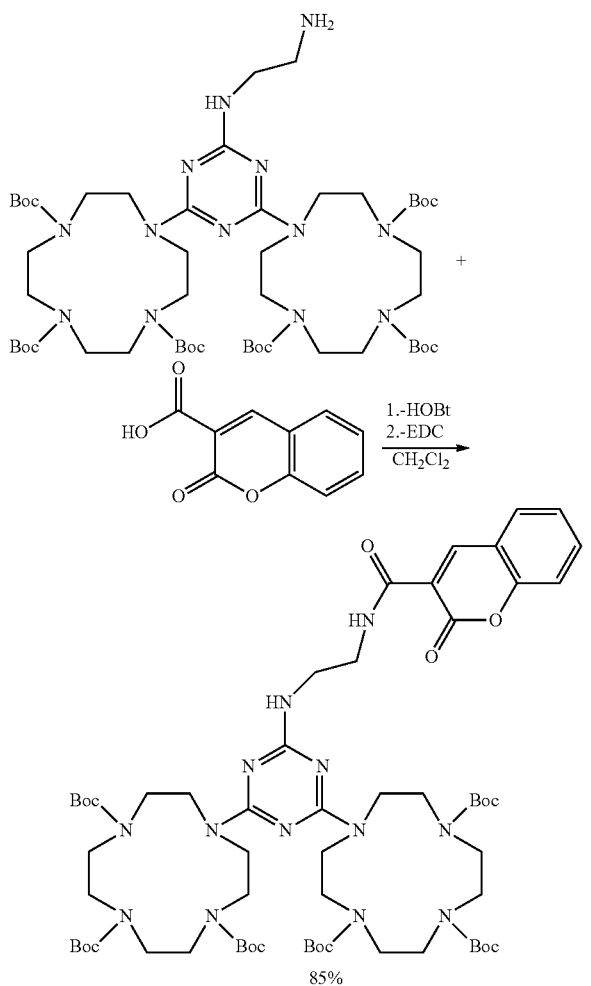

A round bottom flask was charged with 16 (2.2 g, 2.0 mmol), 3 Coumarin-3-carboxylic acid (0.46 g, 2.4 mmol) and HOBt (0.3 g, 2.3 mmol) dissolved everything in CH$_2$Cl$_2$. The reaction was initiated by adding dropwise a solution of 1-Ethyl-3-(3-dimethylaminopropyl)carbodiimide (EDC) (0.5 g, 2.4 mmol) in CH$_2$Cl$_2$. The reaction mixture was stirred overnight washed with a saturated solution of KHCO$_2$ and brine, the organic layer was dried with sodium sulfate, filtered and the solvent removed under reduced pressure. The product was purified by column chromatography 50:50 Hexanes:EtOAc R$_f$=0.6, 85% isolated yield.

H NMR (300 MHz, CDCl$_3$): δ[ppm]=1.4 (s, 54H, CH$_3$-Boc), 2.0 (s, 4H, CH$_2$CH$_2$), 3.3-3.6 (broad, 32H, CH$_2$-cyclen), 5.1 (s, 4H, NH$_2$), 7.2-7.7 (m, 4H, phenyl-coumarin), 8.9 (s, 1H, CHC—C=O, coumarin); $^{13}$C NMR (75 MHz, CDCl$_3$): δ[ppm]=28.6, 28.7, 29.6 (CH$_3$-Boc), 40.1 (CH$_2$CH$_2$), 50.5 (broad, CH$_2$-cyclen), 79.9 ($C_{quat}$, C-Boc), 116.8, 118.7, 125.5, 130.0, 134.3 (ring coumarin), 148.5 (C—O—C=O), 154.6 ($C_{quat}$, C=O-Boc), 160.9 (O=C—C—C=O) 162.2 ($C_{quat}$, triazine-$C_{aryl}$—N), 166.0 ($C_{quat}$, triazine-$C_{aryl}$—N); MS (ESI, CH$_3$CN:H$_2$O+0.1% CH$_2$O$_2$) m/z=1252 [+H]

Preparation of N-(2-((4,6-di(1,4,7,10-tetraazacyclododecan-1-yl)-1,3,5-triazin-2-yl)amino)ethyl)-2-oxo-2H-chromene-3-carboxamide (18)

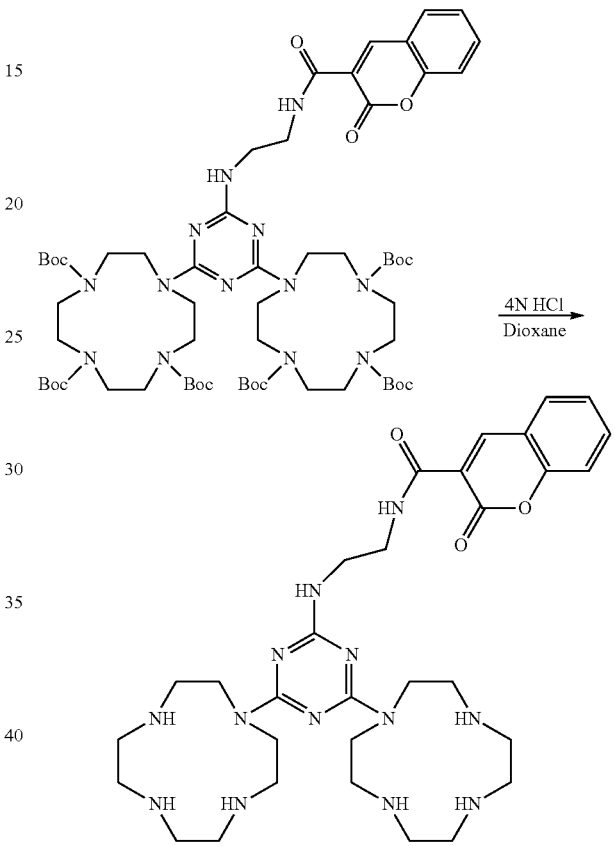

To a solution of 17 (1.2 g, 0.9 mmol) in anhydrous CH$_2$Cl$_2$ was added 4 N HCl in dioxane. The reaction mixture was stirred at room temperature for 1 h. Solvent was removed under reduced pressure and the residue was diluted with EtOAc and washed with 1 N NaOH (3×), water (2×), brine (2×) dried over Na$_2$SO$_4$ filtered and concentrated.

H NMR (300 MHz, CDCl$_3$): δ[ppm]=2.0 (s, 4H, CH$_2$CH$_2$), 3.5-3.7 (broad, 32H, CH$_2$-cyclen), 5.1 (s, 4H, NH$_2$), 7.4-7.7 (m, 4H, phenyl-coumarin), 8.9 (s, 1H, CHC—C=O, coumarin); C NMR (75 MHz, CDCl$_3$): δ[ppm]=40.4 (CH$_2$CH$_2$), 46.0-49.4 (broad, CH$_2$-cyclen), 116.6, 118.6, 125.3, 129.8, 134.0 (ring coumarin), 148.3 (C—O—C=O), 162.2 ($C_{quat}$, triazine-$C_{aryl}$—N), 166.5 ($C_{quat}$, triazine-$C_{aryl}$—N); MS (ESI, CH$_3$CN:H$_2$O+0.1% CH$_2$O$_2$) m/z=652 [+H]

An invention has been provided with several advantages. The interaction of redox active metal ions with amyloid is known to produce ROS that lead to neurological degradation associated with Alzheimer's disease and other neurodegenerative disorders. A molecular system capable of bimodal modulation of the metal-ions in amyloid as well as regulation of ROS would prove useful in combating this disease. Applicants have shown that pyclen, a backbone commonly investigated for contrast agent imaging, may be repurposed as an anti-oxidant chelator for disaggregating amyloid. The anti-oxidant capacity of pyclen was enhanced dramatically via conversion of the pyridine backbone to a pyridol to produce the hydroxylated version of the pyclen molecule with cellular studies showing superior antioxidant capacity while retaining chelation ability to protect amyloid from metal ions aggregation and also disaggregate amyloid aggregates. Direct reactions with $H_2O_2$ show that the pyridol backbone is the key to this ability due to the formation of di-keto species of the hydrated pyclen. Applicants have extended these findings to another family of compounds in the form of "hybrid" heterocyclic amine ligands.

While the invention has been shown in several of its forms, it is not thus limited, but is susceptible to various changes and modifications without departing from the spirit thereof.

What is claimed is:

1. A molecule selected from the group consisting of:

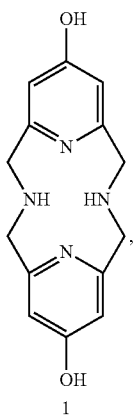
1

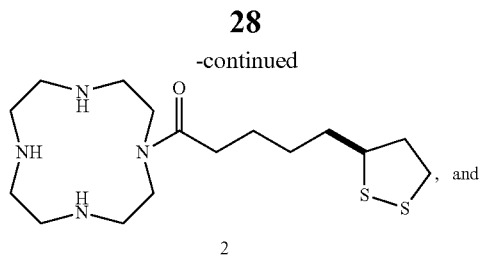
2

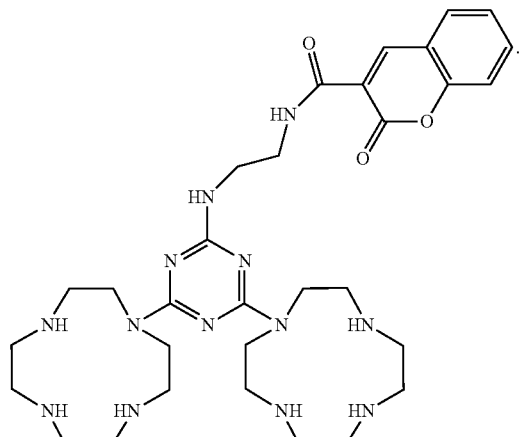
3